(12) United States Patent
Wygrecka et al.

(10) Patent No.: US 11,505,619 B2
(45) Date of Patent: Nov. 22, 2022

(54) USE OF A FXIIA-INHIBITOR IN THE TREATMENT OF RENAL FIBROSIS AND/OR CHRONIC KIDNEY DISEASE

(71) Applicant: CSL LIMITED, Parkville (AU)

(72) Inventors: Malgorzata Wygrecka, Giessen (DE); Marc Nolte, Marburg (DE); Con Panousis, Bundoora (AU)

(73) Assignee: CSL Limited, Parkville (AU)

( * ) Notice: Subject to any disclaimer, the term of this patent is extended or adjusted under 35 U.S.C. 154(b) by 0 days.

(21) Appl. No.: 16/772,207

(22) PCT Filed: Dec. 14, 2018

(86) PCT No.: PCT/AU2018/051333
§ 371 (c)(1),
(2) Date: Jun. 12, 2020

(87) PCT Pub. No.: WO2019/113642
PCT Pub. Date: Jun. 20, 2019

(65) Prior Publication Data
US 2021/0070879 A1 Mar. 11, 2021

(30) Foreign Application Priority Data
Dec. 15, 2017 (EP) .................................. 17207595

(51) Int. Cl.
C07K 16/36 (2006.01)
A61K 47/60 (2017.01)
A61P 13/12 (2006.01)
A61K 38/57 (2006.01)

(52) U.S. Cl.
CPC ............ *C07K 16/36* (2013.01); *A61K 38/57* (2013.01); *A61K 47/60* (2017.08); *A61P 13/12* (2018.01); *C07K 2317/76* (2013.01)

(58) Field of Classification Search
None
See application file for complete search history.

(56) References Cited

U.S. PATENT DOCUMENTS

| | | | |
|---|---|---|---|
| 9,574,013 B2 * | 2/2017 | Gruber | C07K 16/40 |
| 2014/0199361 A1 * | 7/2014 | Panousis | A61P 1/18 |
| | | | 424/422 |

FOREIGN PATENT DOCUMENTS

| | | | |
|---|---|---|---|
| WO | WO 99/036439 | 7/1999 | |
| WO | WO 01/79271 | 10/2001 | |
| WO | WO 2006/066878 | 6/2006 | |
| WO | WO 2008/098720 | 8/2008 | |
| WO | WO 2011/121123 | 10/2011 | |
| WO | WO 2013/113774 | 8/2013 | |
| WO | WO 2014/135694 | 9/2014 | |
| WO | WO-2014135694 A1 * | 9/2014 | A61K 38/57 |
| WO | WO-2014207199 A1 * | 12/2014 | A61K 45/06 |
| WO | WO 2015/193457 | 12/2015 | |
| WO | WO 2017/120397 | 7/2017 | |
| WO | WO 2017/173494 | 10/2017 | |

OTHER PUBLICATIONS

Janeway et al., Immunobiology, 3rd edition, 1997 Garland Publishing Inc., pp. 3:1-3:11.*
Rudikoff et al., Proc Natl Acad Sci USA. Mar. 1982;79(6):1979-83.*
Edwards et al., J Mol Biol. Nov. 14, 2003;334(1):103-18.*
Lloyd et al., Protein Eng Des Sel. Mar. 2009;22(3):159-68. doi: 10.1093/protein/gzn058. Epub Oct. 29, 2008.*
Goel et al., J Immunol. Dec. 15, 2004;173(12):7358-67.*
Kanyavuz et al., Nat Rev Immunol. Jun. 2019;19(6):355-368. doi: 10.1038/S41577-019-0126-7.*
De Maat et al., J Thromb Haemost. Aug. 2016;14(8):1498-506. doi: 10.1111/jth.13383. Epub Aug. 2, 2016. PMID: 27282310.*
Renne et al., Front Immunol. Aug. 22, 2019;10:2011. doi: 10.3389/fimmu.2019.02011. eCollection 2019. PMID: 31507606.*
Mannhalter et al, "Clotting activities and antigen concentrations of contact factors in kidney disease," Thrombosis Research, 1985, 39(4), 475-484.
Chothia et al., "Canonical structures for the hypervariable regions of immunoglobulins," J Mol Biol, 1987, 196, 4, 901-917.
Chothia et al., "Conformations of immunoglobulin hypervariable regions," Nature, 1989, 342, 877-883.
Bork et al., "The immunoglobulin fold structural classification, sequence patterns and common core," J Mol Biol, 1994, 242(4), 309-320.
Al-Lazikani et al., "Standard conformations for the canonical structures of immunoglobulins," J Mol Biol, 1997, 273(4), 927-948.
Honegger et al., "Yet Another numbering scheme for immunoglobulin variable domains: An automatic modeling and analysis tool," J Mol Biol, 2001, 309(3), 657-670.
Campos et al., "Infestin, a thrombin inhibitor presents in *Triatoma infestans* midgut, a Chagas' disease vector: gene cloning, expression and characterization of the inhibitor," Insect Biochemistry and Molecular Biology, 2002, 32(9), 991-997.

(Continued)

*Primary Examiner* — Michael Szperka
(74) *Attorney, Agent, or Firm* — Finnegan, Henderson, Farabow, Garrett & Dunner, LLP

(57) ABSTRACT

The invention relates to an inhibitor of Factor XII (FXII) for use in treating or preventing chronic kidney disease, renal fibrosis, glomerulosclerosis, renal scarring, ischemia/reperfusion injury in native or transplant kidneys and/or acute kidney injury, a kit for use in treating or preventing chronic kidney disease, renal fibrosis, glomerulosclerosis, renal scarring, ischemia/reperfusion injury in native or transplant kidneys, acute kidney injury, renal fibrosis as a result of rejection of a kidney transplant/allograft, and/or fibrosis of a kidney transplant/allograft as a result of rejection or recurrent underlying disease comprising one inhibitor of Factor XII, and an anti-Factor XII (FXII) antibody or antigen binding fragment thereof for use in treating or preventing chronic kidney disease, renal fibrosis, glomerulosclerosis, renal scarring, ischemia/reperfusion injury in native or transplant kidneys and/or acute kidney injury comprising one inhibitor of Factor XII.

17 Claims, 7 Drawing Sheets
Specification includes a Sequence Listing.

(56) References Cited

OTHER PUBLICATIONS

Schaefer et al., "Absence of Decorin Adversely Influences Tubulointerstitial Fibrosis of the Obstructed Kidney by Enhanced Apoptosis and Increased Inflammatory Reaction," American Journal of Pathology, 2002, 160(3), 1181-1191.
Lefranc et al., "IMGT unique numbering for immunoglobulin and T cell receptor variable domains and Ig superfamily V-like domains," Developmental and Comparative Immunology, 2003, 27(1), 55-77.
Campos et al., "Identification and characterization of a novel factor XIIa inhibitor in the hematophagous insect, *Triatoma Infestans* (Hemiptera: Reduviidae)," FEBS Letters, 2004, 577(3), 512-516.
Nahrendorf et al., "Activatable magnetic resonance imaging agent reports myeloperoxidase activity in healing infarcts and noninvasively detects the antiinflammatory effects of atorvastatin on ischemia-reperfusion injury," Circulation, 2008, 117(8), 1153-1160.
Chevalier et al., "Ureteral obstruction as a model of renal interstitial fibrosis and obstructive nephropathy," International Society of Nephrology, 2009, 75, 1145-1152.
Hagedorn et al., "Factor XIIa inhibitor recombinant human albumin infestin-4 abolishes occlusive arterial thrombus formation without affecting bleeding," Circulation, 2010, 121(13), 1510-1517.
Moreth et al., "The proteoglycan biglycan regulates expression of the B cell chemoattractant CXCL13 and aggravates murine lupus nephritis," J Clin Invest, 2010,120(12), 4251-4272.
Jablonska, "Role of intrinsic coagulation pathway in the pathogenesis of idiopathic pulmonary fibrosis," Dissertation, 2010, 109 pages.
Sharma et al., "Pirfenidone for Diabetic Nephropathy," J Am Soc Nephrol, 2011, 22, 1144-1151.

Babelova et al., "Role of Nox4 in murine models of kidney disease," Free Radical Biology and Medicine, 2012, 53, 842-853.
Mercer et al., "Coagulation and coagulation signalling in fibrosis," Biochimica et Biophysica Acta, 2013, 1832(7), 1018-1027.
Zeisberg et al., "Cellular mechanisms of tissue fibrosis. 1. Common and organ-specific mechanisms associated with tissue fibrosis," Am J Physiol Cell Physiol, 2013, 304, C216-C225.
Papageorgio et al., "Coagulation Factor XIIa-kinin-mediated contribution to hypertension of chronic kidney disease," J. Hypertension, 2014, 32(7), 1523-1533.
Nanthakumar et al., "Dissecting fibrosis: therapeutic insights from the small-molecule toolbox," Nature Reviews, 2015, 14, 693-720.
Nugent et al., "HIPK2 is a new drug target for anti-fibrosis therapy in kidney disease." Frontiers in Physiology, 2015, 6(132), 1-5.
Sun et al., "α-Smooth muscle actin is an inconsistent marker of fibroblasts responsible for force-dependent TGFβactivation or collagen production across multiple models of organ fibrosis," Am J Physiol Lung Cell Mol Physiol, 2016, 310, L824-L836.
Xie et al., "Transcription factor TBX4 regulates myofibroblast accumulation and lung fibrosis," The Journal of Clinical Investigation, 2016, 126(8), 3063-3079.
Danobeitia et al., "Complement inhibition attenuates acute kidney injury after ischemia-reperfusion and limits progression to renal fibrosis in mice," PLoS One, 2017, 12(8):e0183701.
Vorlova et al., "Coagulation factor XII induces pro-inflammatory cytokine responses in macrophages and promotes atherosclerosis in mice," Thrombosis and Haemostasis, 2017, 117(1), 176-187.
The extended European search report issued in European Application No. 17207595.4, dated Apr. 17, 2018, 7 pages.
International Search Report issued in PCT/AU2018/051333 and the Written Opinion of the International Searching Authority, dated Feb. 25, 2019, 13 pages.

\* cited by examiner

USE OF A FXIIA-INHIBITOR IN THE TREATMENT OF RENAL FIBROSIS AND/OR CHRONIC KIDNEY DISEASE

This application is the United States national stage entry under 35 U.S.C. § 371 of International Application No. PCT/AU2018/051333, filed on Dec. 14, 2018, which claims priority to European Patent Application No. 17207595.4, filed on Dec. 15, 2017. The contents of these applications are each incorporated herein by reference in their entirety.

FIELD

The present disclosure relates to a method of treating or preventing a renal or kidney disease.

INTRODUCTION

More than 10% of the adult US-population (about 30 million) is suffering from chronic kidney disease (CKD). This prevalence together with a lack of appropriate curative treatments, calls for the development of novel therapeutic strategies in CKD. Renal fibrosis is considered to be the final manifestation of most chronic kidney diseases, independently of their primary etiology. Nearly 99% of the kidney parenchyma consists of the tubulointerstitium. The loss of tubular epithelial cells (TECs) based on enhanced cell death and/or decreased proliferation/regeneration represents the initial and decisive mechanism responsible for driving renal diseases towards chronification and fibrosis. Death of TECs together with hyperactivation of fibroblasts and their differentiation into myofibroblasts, promotes uncontrolled production and accumulation of the extracellular matrix (ECM), thereby replacing functional nephrons by fibrotic scar tissue.

The experimental model of unilateral ureteral obstruction (UUO) has been widely used to study the pathogenesis of tubulointerstitial fibrosis, as the evolution of fibrosis after ureteral obstruction is highly reproducible and recapitulates in an accelerated manner the sequence of pathogenetic events that occur in human renal fibrosis. In contrast to idiopathic pulmonary fibrosis, infiltrating macrophages are one of the main features of the renal interstitial fibrosis. Macrophages can affect kidney injury through the following mechanisms: i) boosting the inflammatory response by releasing an abundance of proinflammatory mediators, ii) macrophage-derived reactive oxygen species and TNF-α can trigger apoptosis and necrosis of TECs, therefore magnifying the renal injury, and iii) overproduction of profibrotic cytokines and growth factors by macrophages may stimulate proliferation of fibroblasts and their differentiation to α-smooth muscle actin (SMA)-positive myofibroblasts thereby inducing abnormal wound healing and finally fibrosis. Accumulating evidence suggests that the degree of macrophage infiltration strongly correlates with the severity of renal damage. The detrimental role of macrophages in the pathogenesis of kidney diseases is also supported by the studies demonstrating that depletion of macrophages halts the development of crescentic glomerulonephritis and adoptive transfer of bone marrow-derived macrophages aggravates renal injury in the same disease model. The UUO model is e.g. described in Chevalier et al., Kidney International (2009), 75, 1145-1152 (doi:10.1038/ki.2009.86).

The contact system, or plasma kallikrein-kinin system, consists of three serine proteases: Hageman factor (coagulation factor XII, FXII), factor XI (FXI), and plasma kallikrein (PKLK), and the nonenzymatic co-factor high molecular weight kininogen (HK). Activation of the contact system occurs upon exposure of FXII to negatively charged surfaces such as kaolin, dextran sulphate, endotoxin, extracellular RNA, polyphosphates, and heparin. In this environment FXII is converted into a two-chain, active protease, FXIIa. FXIIa initiates the intrinsic blood coagulation pathway via activation of factor XI (FXI). Recent data, however, support the notion that FXII is dispensable for physiologic haemostasis, and demonstrate an essential role of FXII in pathologic thrombosis. Furthermore, FXIIa converts prekallikrein to kallikrein, which in turn activates additional FXII and liberates bradykinin (BK) from high-molecular weight kininogen (HK). In addition, FXII stimulates the proliferation of endothelial cells in an uPAR-dependent manner.

Prior art publication WO 2006/066878 relates to the use of an anti-FXII antibody for inhibiting coagulation factor XII, as well as the use of a corresponding antibody or inhibitor in the treatment or prophylaxis of disorders related to venous or arterial thrombus formation, i.e. as an anti-thrombotic agent. Prior art publication WO 2011/121123 A1 relates to the use of Factor XII inhibitors for treating interstitial lung disease. The dissertation "Role of Instrinsic Coagulation Pathway in the Pathogenesis of Idiopathic Pulmonary Fibrosis" of Ewa Jablonska, 29 Nov. 2010, VVB Laufersweiler, Giessen (ISBN: 978-3-8359-5693-3) relates to FXI/FXII in the context of the coagulation pathway in the pathogenesis of idiopathic pulmonary fibrosis (IPF). Prior art publication WO 2015/193457 A1 relates to the use of a Factor XII inhibitor for treating a neurotraumatic disorder. Vorlova et al. in Thromb. Haemost. 2017 Jan. 5; 117(1): 176-187 (doi: 10.1160/TH16-06-0466; Epub 2016 Oct. 27) discuss targeting of FXII as an approach for treating cardiovascular disease.

So far, the role of FXII in the development of renal fibrosis and/or chronic kidney disease (CKD) has not been assessed.

Known small molecules or agents undergoing or having undergone clinical trials in relation to kidney or renal fibrosis are associated with different targets and/or mechanisms (Nanthakumar et al., Nature Reviews 2015, 693-720, doi: 10.1038/nrd4592). While pirfenidone is able to prevent kidney fibrosis in rodents, these benefits have not yet been confirmed in renal patients. In a study with 77 patients with kidney disease, pirfenidone improved renal function but failed to significantly reduce proteinurea, suggesting that pirfenidone improves renal function but does not improve podocyte injury. Several key signalling pathways that mediate renal fibrosis have been identified, but currently none of the drugs targeting these pathways have been proven to be effective in anti-fibrosis therapy for kidney disease in large clinical trials, and novel targets keep getting suggested (Nugent et al., frontiers in physiology 2015 (6), Article 132, doi: 10.3389/fphys.2015.00132).

The impact of human C1 inhibitor (C1 INH) on the early inflammatory response to ischaemia-reperfusion injury (IRI) and the subsequent progression to fibrosis in mice has been investigated in a study, wherein it was observed that animals receiving C1-INH prior to reperfusion had a significant improvement in survival rate along with superior renal function when compared to vehicle (PBS) treated counterparts. Findings in this context were found to indicate that intravenous delivery of C1-INH prior to ischemic injury protects kidneys from inflammatory injury and subsequent progression to fibrosis. The authors conclude that early complement blockade in the context of IRI constitutes an effective strategy in the prevention of fibrosis after ischemic acute kidney injury (Danobeitia J. S, Ziemelis M, Ma X, Zitur L J, Zens T, Chlebeck P J, et al. (2017), Complement inhibition attenuates acute kidney injury after ischemia-reperfusion and limits progression to renal fibrosis in mice; PLoS ONE 12(8): e0183701. https://doi.org/10.1371/journal.pone.0183701).

Despite the aforementioned efforts, there are currently no approved medicines for the treatment of renal fibrosis and/or chronic kidney disease (CKD). There is thus an unmet clinical need for antifibrotic strategies, which will preferably prevent uncontrolled TEC death, promote tubular proliferation/regeneration and inhibit fibroblast activation.

SUMMARY

To meet the aforementioned need, the present invention provides
an inhibitor of Factor XII (FXII) for use in treating or preventing of,
a kit for use in the treatment and prevention of, and
an anti-Factor XII (FXII) antibody or antigen binding fragment thereof for use in the treatment and prevention of
chronic kidney disease and/or renal fibrosis in a subject, in particular in a human or animal subject, in particular wherein the chronic kidney disease and/or renal fibrosis is a result of and/or is associated with one or more of the following: glomerulosclerosis, renal scarring, ischemia/reperfusion injury in kidneys, acute kidney injury, rejection of a kidney transplant/allograft, a recurrent underlying disease, and/or an inflammatory kidney disease related to FXII/FXIIa-mediated complement formation, selected from the group not limited to Nephritides, Lupus-Nephritis, C3-Glomerulonephritis, Dense Deposit Disease, atypical haemolytic-uremic syndrome, post-streptococcal glomerulonephritis, Henoch-Schoenlein Purpura and antibody-mediated rejection of a kidney transplant.

In the context of the present invention and throughout the whole of the specification and the claims, the term "inhibitor of Factor XII" shall be understood so as to not encompass C1INH, i.e. "with the proviso that the inhibitor of Factor XII is not C1 INH".

In producing the present invention, the inventors have studied the effects of inhibiting Factor XII (FXII) in a mouse model of renal fibrosis using the above-mentioned experimental model of unilateral ureteral obstruction (UUO). The inventors found that FXII inhibition in experimental renal fibrosis
(i) markedly reduces the abundance of extracellular matrix proteins,
(ii) neither affects macrophage accumulation nor cytokine production at an early stage,
(iii) leads to a marked reduction in the number of apoptotic renal tubular epithelial cells at an early and a late stage of the disease,
(iv) leads to an increase in the number of proliferating renal tubular epithelial cells at an early and late stage of the disease, and
(v) attenuates body weight loss.

The inventors demonstrated these effects by administering an inhibitor of FXII to an accepted animal model of renal fibrosis that recapitulates in an accelerated manner the sequence of pathogenetic events that occur in human renal fibrosis.

The findings by the inventors provide the basis for methods for treating or preventing renal fibrosis and/or chronic kidney disease (CKD) in a subject by inhibiting FXII. The findings by the inventors also provide the basis for an inhibitor of FXII for use in treating or preventing renal fibrosis and/or CKD in a subject.

For example, the present disclosure provides a method for treating renal fibrosis and/or CKD in a subject comprising administering to the subject an inhibitor of FXII. In another example, the disclosure provides a method for preventing renal fibrosis in a subject, the method comprising administering to the subject an inhibitor of FXII.

In an alternative example, the present disclosure provides an inhibitor of FXII for use in treating renal fibrosis in a subject. In another example, the disclosure provides an inhibitor of FXII for use in preventing renal fibrosis in a subject.

The inventors have also found that they can reduce the progression of renal fibrosis in a subject. Accordingly, the present disclosure additionally provides a method for or an inhibitor of FXII for use in reducing the progression of renal fibrosis in a subject. For example, the present disclosure provides a method for or an inhibitor of FXII for use in reducing the risk of or preventing renal fibrosis in a subject.

In one example, the inhibitor of FXII is a direct inhibitor. In one example, the inhibitor of FXII binds to FXII and/or FXIIa. In one example, the inhibitor of FXII binds to FXII and/or FXIIa and inhibits the activity of FXII and/or FXIIa. For example, the inhibitor of FXII binds to FXIIa and inhibits the activity of FXIIa. In another example, the inhibitor of FXII binds to FXII and inhibits FXII activation. In one example, the activity of FXII and/or FXIIa is inhibited by at least about 50%, 60%, 65%, 70%, 75%, 80%, 85%, 90%, or 95%, respectively. For example, the activity of FXII and/or FXIIa is inhibited by respectively about 60%, 65%, 70%, 75%, 80%, 85%, 90%, 95%, 96%, 97%, 98%, 99%, or 100%. Methods for determining the activity of FXII and/or FXIIa are known in the art and/or described herein.

In one example, the inhibitor of FXII is a serine protease inhibitor. For example, the FXII inhibitor is Infestin-4. In another example, the FXII inhibitor is SPINK-1. In a further example, the FXII inhibitor is an Infestin-4 or SPINK-1 variant.

In one example, the inhibitor of FXII is not a serine protease inhibitor. For example, the inhibitor of FXII is not Infestin-4. For example, the inhibitor of FXII is not a variant of Infestin-4. In one example, the inhibitor of FXII is not SPINK-1. For example, the inhibitor of FXII is nota variant of SPINK-1.

In one example, the method of or the inhibitor of FXII for use in the present disclosure comprises administering an inhibitor of FXII, wherein the inhibitor comprises:
(i) the wild type Infestin-4 polypeptide sequence (SEQ ID NO: 1), or a polypeptide sequence comprising:
  (a) SEQ ID NO: 1 modified to contain 1-5 amino acid mutations outside of N-terminal amino acid positions 2-13 of SEQ ID NO: 1; and/or
  (b) an identity of at least 70% to SEQ ID NO: 1 and retaining six conserved cysteine residues from SEQ ID NO: 1; or
(ii) a wild-type SPINK-1 polypeptide sequence (SEQ ID NO: 2), or a polypeptide sequence comprising:
  (a) SEQ ID NO: 2 mutated to replace N-terminal amino acid positions 2-13 with the N-terminal amino acids 2-13 of SEQ ID NO: 1; and optionally further modified to contain 1-5 additional amino acid mutations that increase the homology of the polypeptide sequence to the sequence of SEQ ID NO: 1; and/or
  (b) an identity of at least 70% to SEQ ID NO: 2 and retaining six conserved cysteine residues from SEQ ID NO: 2; or (iii) one of SPINK-1 mutants K1 (SEQ ID NO: 3), K2 (SEQ ID NO: 4), or K3 (SEQ ID NO: 5).

In one example, the inhibitor of FXII comprises the sequence of the serine protease inhibitor Infestin-4. For example, the inhibitor of FXII comprises the sequence set forth in SEQ ID NO: 1.

In one example, the inhibitor of FXII comprises a modified Infestin-4. For example, the inhibitor of FXII comprises the sequence set forth in SEQ ID NO: 1 modified to contain 1-5 amino acid mutations outside of N-terminal amino acid positions 2-13 of SEQ ID NO: 1.

In another example, the inhibitor of FXII comprises a sequence with at least 70% identity to the sequence set forth in SEQ ID NO: 1 and retaining six conserved cysteine residues from SEQ ID NO: 1. For example, the inhibitor of FXII has an identity of about 75% to SEQ ID NO: 1, or an identity of about 80% to SEQ ID NO: 1, or an identity of about 85% to SEQ ID NO: 1, or an identity of about 90% to SEQ ID NO: 1, or an identity of about 95% to SEQ ID NO: 1, or an identity of about 98% to SEQ ID NO: 1, or an identity of about 99% to SEQ ID NO: 1.

In one example, the inhibitor of FXII comprises the sequence of the serine protease inhibitor SPINK-1. For example, the inhibitor of FXII comprises the sequence set forth in SEQ ID NO: 2.

In another example, the inhibitor of FXII comprises the sequence set forth in SEQ ID NO: 2 mutated to replace N-terminal amino acid positions 2-13 with the N-terminal amino acids 2-13 of SEQ ID NO: 1; and optionally further modified to contain 1-5 additional amino acid mutations that increase the homology of the polypeptide sequence to sequence of SEQ ID NO: 1.

In another example, the inhibitor of FXII comprises a sequence with at least 70% identity to the sequence set forth in SEQ ID NO: 2 and retaining six conserved cysteine residues from SEQ ID NO: 2. For example, the inhibitor of FXII has an identity of about 75% to SEQ ID NO: 2, or an identity of about 80% to SEQ ID NO: 2, or an identity of about 85% to SEQ ID NO: 2, or an identity of about 90% to SEQ ID NO: 2, or an identity of about 95% to SEQ ID NO: 2, or an identity of about 98% to SEQ ID NO: 2, or an identity of about 99% to SEQ ID NO: 2.

In one example, the inhibitor of FXII is a protein comprising a variable region fragment (Fv). For example, the protein is selected from the group consisting of:
(i) a single chain Fv fragment (scFv);
(ii) a dimeric scFv (di-scFv); or
(iv) a diabody (i.e. a bispecific antibody);
(v) a triabody (i.e. a trispecific antibody);
(vi) a tetrabody (i.e. a tetraspecific antibody);
(vii) a Fab;
(viii) a F(ab')$_2$;
(ix) a Fv;
(x) one of (i) to (ix) linked to a constant region of an antibody, Fc or a heavy chain constant domain ($C_H$) 2 and/or $C_H$3; or
(xi) an antibody.

In one example, an inhibitor of FXII is an antibody. For example, the antibody is an anti-FXII antibody. In another example, the antibody is an anti-FXIIa antibody.

Exemplary antibodies are full-length and/or naked antibodies.

In one example, the inhibitor of FXII is a protein that is recombinant, chimeric, CDR grafted, humanized, synhumanized, primatized, deimmunized or human.

In one example, the antibody is an IgG antibody.

In one example, the anti-FXII antibody comprises a heavy chain variable region ($V_H$) comprising a sequence set forth in SEQ ID NO: 6.

In one example, the anti-FXII antibody comprises a light chain variable region ($V_L$) comprising a sequence set forth in SEQ ID NO: 7.

In one example, the anti-FXII antibody comprises a $V_H$ comprising a sequence set forth in SEQ ID NO: 6 and a $V_L$ comprising a sequence set forth in SEQ ID NO: 7.

In one example, the anti-FXII antibody comprises a variable region comprising the complementary determining regions (CDRs) of the $V_H$ and/or the $V_L$ of SEQ ID NO: 6 and SEQ ID NO: 7.

In one example, the protein or antibody is any form of the protein or antibody encoded by a nucleic acid encoding any of the foregoing proteins or antibodies, such as a variant missing an encoded C-terminal lysine residue, a deamidated variant and/or a glycosylated variant and/or a variant comprising a pyroglutamate, e.g., at the N-terminus of a protein and/or a variant lacking a N-terminal residue.

In one example, the anti-FXII antibody comprises:
(i) a $V_H$ comprising:
  (a) a sequence set forth in SEQ ID NO: 6; or
  (b) a CDR1 comprising a sequence set forth in SEQ ID NO: 8; a CDR2 comprising a sequence set forth in SEQ ID NO: 10; and a CDR3 comprising a sequence set forth in SEQ ID NO: 12; or (c) a CDR1 comprising a sequence set forth in SEQ ID NO: 8; a CDR2 comprising a sequence set forth in SEQ ID NO: 9; and a CDR3 comprising a sequence set forth in SEQ ID NO: 11; and/or
(ii) a $V_L$ comprising:
  (a) a sequence set forth in SEQ ID NO: 7; or
  (b) a CDR1 comprising a sequence set forth in SEQ ID NO: 13; a CDR2 comprising a sequence set forth in SEQ ID NO: 14; and a CDR3 comprising a sequence set forth in SEQ ID NO: 16; or
  (c) a CDR1 comprising a sequence set forth in SEQ ID NO: 13; a CDR2 comprising a sequence set forth in SEQ ID NO: 14; and a CDR3 comprising a sequence set forth in SEQ ID NO: 15.

In one example, the anti-FXII antibody comprises:
(i) a $V_H$ comprising:
  (a) a CDR1 comprising a sequence set forth in SEQ ID NO: 8;
  (b) a CDR2 comprising a sequence set forth in SEQ ID NO: 10; and
  (c) a CDR3 comprising a sequence set forth in SEQ ID NO: 12; and/or
(ii) a $V_L$ comprising:
  (a) a CDR1 comprising a sequence as set forth in SEQ ID NO: 13;
  (b) a CDR2 comprising a sequence as set forth in SEQ ID NO: 14; and
  (c) a CDR3 comprising a sequence as set forth in SEQ ID NO: 16.

In one example, the anti-FXII antibody comprises:
(i) a $V_H$ comprising:
  (a) a CDR1 comprising a sequence set forth in SEQ ID NO: 8;
  (b) a CDR2 comprising a sequence set forth in SEQ ID NO: 9; and
  (c) a CDR3 comprising a sequence set forth in SEQ ID NO: 11; and/or
(ii) a $V_L$ comprising:
  (a) a CDR1 comprising a sequence as set forth in SEQ ID NO: 13;

(b) a CDR2 comprising a sequence as set forth in SEQ ID NO: 14; and
(c) a CDR3 comprising a sequence as set forth in SEQ ID NO: 15.

In one example, the anti-FXII antibody comprises:
(i) a $V_H$ comprising
  (a) a CDR1 set forth in SEQ ID NO: 8;
  (b) a CDR2 set forth in SEQ ID NO: 10 wherein the X at position 3 is D, the X at position 4 is I, the X at position 5 is P, the X at position 6 is T, the X at position 7 is K, and the X at position 8 is G; and
  (c) a CDR3 set forth in SEQ ID NO: 11; and/or
(ii) a $V_L$ comprising
  (a) a CDR1 set forth in SEQ ID NO: 13;
  (b) CDR2 set forth in SEQ ID NO: 14; and
  (c) a CDR3 set forth in SEQ ID NO: 15.

For example, the anti-FXII antibody comprises a $V_H$ comprising a sequence set forth in SEQ ID NO: 18 and a $V_L$ comprising a sequence set forth in SEQ ID NO: 19.

In one example, the anti-FXII antibody comprises lambda light chain constant regions.

In one example, the anti-FXII antibody comprises IgG4 or stabilized IgG4 constant regions. For example, the stabilized IgG4 constant regions comprise a proline at position 241 of the hinge region according to the system of Kabat (Kabat et al., Sequences of Proteins of Immunological Interest Washington D.C. United States Department of Health and Human Services, 1987 and/or 1991).

In one example, the anti-FXII antibody is within a composition. For example, the composition comprises a protein comprising an antibody variable region or a $V_H$ or a $V_L$ or an antibody as described herein. In one example, the composition additionally comprises one or more variants of the protein or antibody. For example, that comprises a variant missing an encoded C-terminal lysine residue, a deamidated variant and/or a glycosylated variant and/or a variant comprising a pyroglutamate, e.g., at the N-terminus of a protein and/or a variant lacking a N-terminal residue, e.g., a N-terminal glutamine in an antibody or V region and/or a variant comprising all or part of a secretion signal. Deamidated variants of encoded asparagine residues may result in isoaspartic, and aspartic acid isoforms being generated or even a succinamide involving an adjacent amino acid residue. Deamidated variants of encoded glutamine residues may result in glutamic acid. Compositions comprising a heterogeneous mixture of such sequences and variants are intended to be included when reference is made to a particular amino acid sequence.

In one example, of any method or an inhibitor of FXII for use described herein, the inhibitor of FXII is linked to a fusion partner. For example, the fusion partner comprises polyethylene glycol (PEG) or a half-life enhancing polypeptide.

In one example, the inhibitor of FXII is linked to the fusion partner directly. In another example, the inhibitor of FXII is linked to the fusion partner via a linker. For example, the inhibitor of FXII is linked to a half-life enhancing polypeptide directly. In another example, the inhibitor of FXII is linked to a half-life enhancing polypeptide via a linker. In one example, the inhibitor of FXII is linked to the PEG directly. In another example, the inhibitor of FXII is linked to the PEG via a linker.

In one example, the linker is an intervening peptidic linker. For example, the linker is a cleavable linker.

In one example, the half-life enhancing polypeptide is selected from the group consisting of albumin, afamin, alpha-fetoprotein, vitamin D binding protein, human albumin, an immunoglobulin, and an Fc of an IgG. For example, the half-life enhancing polypeptide is albumin.

In one example, the inhibitor of FXII is a fusion protein comprising human albumin linked to a FXII inhibitor via a linker peptide.

In one example, the inhibitor of FXII is administered parenterally. For example, the inhibitor of FXII is administered intravenously, or subcutaneously, or intrathecal. In one example, the inhibitor of FXII is administered subcutaneously. In another example, the inhibitor of FXII is administered intravenously.

In one example of any method described herein, the inhibitor of FXII is administered to the subject in one or more doses. For example, the inhibitor of FXII is administered to the subject:
(i) in a single dose; or
(ii) in a plurality of doses; or
(iii) as a continuous infusion or application.

In one example, the inhibitor of FXII is administered to the subject in a single dose.

In one example, the inhibitor of FXII is administered to the subject in a plurality of doses. For example, the inhibitor of FXII is administered to the subject as two doses, or three doses, or four doses, or five doses or more. For example, administration of each dose of the inhibitor of FXII is separated by a period of hours. For example, administration of each dose of the inhibitor of FXII is separated by the period of about 1 hour, or about 2 hours, or about 3 hours, or about 4 hours, or about 6 hours, or about 8 hours, or about 12 hours, or about 16 hours, or about 20 hours, or about 24 hours.

For example, administration of each dose of the inhibitor of FXII is separated by a period of days. For example, administration of each dose of the inhibitor of FXII is separated by the period of about 1 day, or about 2 days, or about 3 days, or about 4 days, or about 5 days, or about 6 days, or about 7 days.

In one example, administration of each dose of the inhibitor of FXII is separated by at least 14 days or at least 28 days.

For example, administration of each dose of the inhibitor of FXII is separated by a period of weeks. For example, administration of each dose of the inhibitor of FXII is separated by the period of about 1 week, or about 2 weeks, or about 3 weeks, or about 4 weeks, or about 5 weeks, or about 6 weeks.

In one example, administration of each dose of the inhibitor of FXII is separated by at least one month.

In one example, the length of time between administrations of the inhibitor of FXII is the same throughout the course of administration. In one example, the length of time between administrations of the inhibitor of FXII is different throughout the course of administration. For example, the inhibitor of FXII is administered on a weekly basis at the commencement of therapy and then on a monthly basis following a predetermined number of doses. In one example, the length of time between administrations of the inhibitor of FXII is variable.

In one example, the inhibitor of FXII is administered to the subject as a continuous dose. For example, the inhibitor of FXII is administered to the subject as a continuous infusion over a period of time. For example, the inhibitor of FXII is administered over a period of between about 1 minute to about 24 hours. For example, the inhibitor of FXII is administered over a period of about 10 minutes to about 12 hours, or about 10 minutes to about 6 hours, or about 10 minutes to about 5 hours, or about 10 minutes to about 4 hours, or about 10 minutes to about 3 hours, or about 10 minutes to about 2 hours, or about 10 minutes to about 1 hour, or about 30 minutes.

In one example, the inhibitor of FXII is administered a plurality of times. For example, the inhibitor of FXII is administered one or more times. For example, the inhibitor of FXII is administered until the renal fibrosis is treated or prevented. For example, the inhibitor of FXII is administered for a period of days to months. For example, the inhibitor of FXII is administered for about one day, or about 2 days, or about 3 days, or about 4 days, or about 5 days, or about 6 days, or about 1 week, or about 2 weeks, or about 4 weeks, or about six weeks, or about 2 months.

In one example, the inhibitor of FXII is administered in a therapeutically or prophylactically effective amount. For example, the inhibitor of FXII is administered to the subject at a dose of about 0.01 mg/kg to about 1000 mg/kg. For example, the inhibitor of FXII is administered at a dose of about 0.01 mg/kg bodyweight, or about 0.1 mg/kg bodyweight, or about 1 mg/kg bodyweight, or about 50 mg/kg bodyweight, or about 100 mg/kg bodyweight, or about 200 mg/kg bodyweight, or about 500 mg/kg bodyweight, or about 1000 mg/kg bodyweight. For example, the inhibitor of FXII is administered at a dose of about 0.001 mg/kg to about 100 mg/kg body weight, or about 0.01 mg/kg to about 100 mg/kg, or about 0.01 mg/kg to about 50 mg/kg, or about 0.1 mg/kg to about 30 mg/kg, or about 0.1 mg/kg to about 10 mg/kg, or about 0.1 mg/kg to about 5 mg/kg, or about 0.1 mg/kg to about 2 mg/kg or about 0.1 mg/kg to about 1 mg/kg. In one example, the inhibitor of FXII is administered at a dose ranging from about 0.01 mg/kg to about 1000 mg/kg, or about 0.1 mg/kg to about 1000 mg/kg, or about 1 mg/kg to about 1000 mg/kg, or about 1 mg/kg to about 500 mg/kg, or about 10 mg/kg to about 200 mg/kg, or about 10 mg/kg to about 100 mg/kg, or about 50 mg/kg to about 500 mg/kg, or about 50 mg/kg to about 200 mg/kg, or about 100 mg/kg to about 200 mg/kg. In one example, the inhibitor of FXII is administered at a dose of about 10 mg/kg. In one example, the inhibitor of FXII is administered at a dose of about 20 mg/kg.

In one example, the subject has renal fibrosis and/or chronic kidney disease (CKD). In one example, the subject has been diagnosed as suffering from renal fibrosis and/or CKD. In one example, the subject is receiving treatment for renal fibrosis and/or CKD. In one example, the subject is receiving treatment for a renal fibrosis and/or CKD associated condition (e.g. diabetic nephropathy, hypertensive nephropathy, glomerulonephritis, glomerulosclerosis, interstitial nephritis). In one example, the patient is receiving treatment for a native or allograft kidney fibrosis and/or CKD. For example, the subject is receiving treatment with an ACE-inhibitor, an antihypertensive, a corticosteroid, an immunosuppressive agent (Azathioprine, MMF, Cyclophosphamide, Rituximab).

In one example, the subject is receiving treatment in the form of dialysis or hemodialysis. In one example the subject is receiving treatment with a RAAS-inhibitor.

In one example of any method or an inhibitor of FXII for use described herein, the subject is at risk of developing renal fibrosis and/or CKD. In this regard, the inhibitor of FXII is used in a preventative or prophylactic manner or can be said to be used in a primary preventative manner. An exemplary subject at risk of developing renal fibrosis and/or CKD suffers from diabetes. For example, the diabetes is type 2 diabetes.

Additional or alternative characteristics of a subject at risk of suffering from renal fibrosis and/or CKD include one or more of the following characteristics:

Diabetic Nephropathy

Hypertensive Nephropathy

Glomerulonephritides

Lupus-Nephritis

Renal Vasculitis

Glomerulosclerosis

Interstitial Nephritis

Autosomal Dominant Polycystic Kidney Disease

Alport-Syndrome

Analgesic Nephropathy

Kidney allograft injury related to ischemia reperfusion or rejection

In one example, a subject with hypertensive nephropathy (nephrosclerosis) at risk of developing renal fibrosis and/or chronic kidney disease (CKD) is treated with the inhibitor of FXIIa to suppress fibrogenesis.

In one example, a subject with chronic glomerulonephritis at risk of developing renal fibrosis and/or CKD is treated with the inhibitor of FXII to prevent kidney fibrosis.

In one example, a subject suffering from Alport syndrome at risk of developing renal fibrosis and/or CKD is treated with the inhibitor of FXII to reduce renal fibrosis.

Patients suffering from renal vasculitis have intensive renal inflammation both in glomeruli and in the tubulo-interstitium with elevated levels of acute phase inflammatory markers: Increased levels of C-reactive protein and IL-6 in the circulation.

In one example of any method described herein, the inhibitor of FXII is administered to the subject before or after the onset of renal fibrosis and/or CKD. For example, the inhibitor of FXII is administered prophylactically or therapeutically. In one example, the inhibitor is administered to the subject prophylactically. In one example, the inhibitor is administered to the subject therapeutically.

Each year approximately 100,000 CKD patients need to start renal replacement therapy in the US because of end stage renal fibrosis irrespective of the underlying renal disease. The present disclosure provides a method for reducing the risk of having to undergo dialysis and/or a kidney transplant by performing a method described herein.

The inhibitor of FXII is administered to patients with diabetic nephropathy in an amount sufficient to elicit the following effects: Reduction of proteinuria and slowing the loss of glomerular filtration rate (GFR).

The inhibitor of FXII is administered in patients suffering from early glomerulosclerosis before the development of renal fibrosis and/or CKD in order to prevent renal fibrosis with end stage renal disease. In a group of patients the inhibitor of FXII is administered after the development of renal fibrosis and/or CKD in order to investigate whether the further loss of GFR can be slowed.

In a group of patients with diabetic nephropathy the inhibitor of FXIIa is administered after the onset of symptoms of renal fibrosis and/or chronic kidney disease (CKD) in order to examine whether proteinuria can be reduced. In a further group of patients with diabetic nephropathy the inhibitor of FXII is administered at a dose that alleviates or reduces one or more of the symptoms of renal fibrosis and/or CKD, such as proteinuria and loss of GFR.

Clinical signs and symptoms of renal fibrosis and/or CKD are known to those skilled in the art. They include:
Hypertension
Volume overload
Anemia
Secondary or tertiary hyperparathyroidism
Metabolic acidosis
Hyperkalemia
Pruritus
Uremic encelopathy Methods of treatment or inhibitors of FXII for use described herein may additionally reduce the need of administering corticosteroids and other immunosuppressive agents (Azathioprine, MMF, Cyclophosphamide, Rituximab) for preventing and/or treating renal fibrosis and/or CKD.

The present disclosure also provides a composition comprising an inhibitor of FXII for use in treating or preventing renal fibrosis and/or CKD in a subject in need thereof. The present disclosure also provides use of an inhibitor of FXII in the manufacture of a medicament for treating or preventing renal fibrosis and/or CKD in a subject.

The present disclosure also provides a kit comprising at least one inhibitor of FXII packaged with instructions for use in treating or preventing renal fibrosis and/or CKD in a subject. Optionally, the kit additionally comprises a therapeutically active compound or drug.

The present disclosure also provides a kit comprising at least one inhibitor of FXII packaged with instructions to administer the inhibitor of FXII to a subject who is suffering from or at risk of suffering from renal fibrosis and/or CKD, optionally, in combination with a therapeutically active compound or drug.

Exemplary effects of renal fibrosis and/or chronic kidney disease (CKD) and inhibitors of FXII are described herein and are to be taken to apply mutatis mutandis to the examples of the disclosure set out in the previous five paragraphs.

An inventor has also produced an inhibitor of FXII, e.g., an anti-FXII antibody or antigen binding fragment thereof suitable for use in treating a human subject. This inhibitor is an affinity matured human antibody that has been modified to make most, but not all, residues in the framework regions the same as those in a germline human antibody thereby reducing the potential for immunogenicity. This antibody is also capable of inhibiting FXIIa and has good manufacturability characteristics. Thus, the present disclosure also provides an anti-FXII antibody or antigen binding fragment thereof, wherein the anti-FXII antibody comprises a $V_H$ comprising a sequence set forth in SEQ ID NO: 18 and a $V_L$ comprising a sequence set forth in SEQ ID NO: 19.

In one example, the anti-FXII antibody comprises lambda light chain constant regions. In one example, the anti-FXII antibody comprises IgG4 or stabilized IgG4 constant regions. For example, the stabilized IgG4 constant regions comprise a proline at position 241 of the hinge region according to the system of Kabat (Kabat et al., Sequences of Proteins of Immunological Interest Washington D.C. United States Department of Health and Human Services, 1987 and/or 1991).

In one example, the anti-FXII antibody comprises a heavy chain comprising a sequence set forth in SEQ ID NO: 20 and a light chain comprising a sequence set forth in SEQ ID NO: 21. In one example, the disclosure provides a composition comprising the anti-FXII antibody or antigen binding fragment and a carrier, e.g., a pharmaceutically acceptable carrier. In one example, the composition additionally comprises one or more variants of the protein or antibody. For example, that comprises a variant missing an encoded C-terminal lysine residue, a deamidated variant and/or a glycosylated variant and/or a variant comprising a pyroglutamate, e.g., at the N-terminus of a protein and/or a variant lacking a N-terminal residue, e.g., a N-terminal glutamine in an antibody or V region and/or a variant comprising all or part of a secretion signal. Deamidated variants of encoded asparagine residues may result in isoaspartic, and aspartic acid isoforms being generated or even a succinamide involving an adjacent amino acid residue. Deamidated variants of encoded glutamine residues may result in glutamic acid. Compositions comprising a heterogeneous mixture of such sequences and variants are intended to be included when reference is made to a particular amino acid sequence.

The present disclosure also provides the anti-FXII antibody or antigen binding fragment thereof for medical use.

The present disclosure also provides a method for treating or preventing a disorder in a subject, the method comprising administering the anti-FXII antibody or antigen binding fragment thereof, wherein the disorder is selected from the group consisting of renal diseases related to FXII/FXIIa-mediated complement activation.

Inflammatory kidney diseases related to FXII/FXIIa-mediated complement activation:
Lupus-Nephritis
C3-Glomerulonephritis
Dense Deposit Disease
Atypical hemolytic-uremic syndrome
Post-Streptococcal Glomerulonephritis
Henoch-Schoenlein Purpura
Antibody-Mediated Rejection of a kidney transplant Patients suffering from these above-mentioned kidney diseases related to FXII/FXIIa-induced complement activation will be selected for treatment with the FXII/FXIIa-inhibitor.

For patients with hereditary Nephritis no effective treatment of the renal inflammation and subsequent fibrosis is available. These patients will be treated with an inhibitor of FXIIa or an anti-FXII antibody.

Patients undergoing extracorporeal treatments (Hemodialysis, plasmapheresis, cascade filtration, and lipidapheresis) are exposed to devices containing negatively charged artificial membranes, which may cause FXII/FXIIa-mediated kinin formation and complement activation. During and/or after the contact of the subject's blood with the artificial surface during and/or after a medical procedure performed on said human subject and said antibody or antigen-binding fragment thereof is administered before and/or during and/or after said medical procedure, wherein
(i) the artificial surface is exposed to at least 100% of the blood volume of the subject and the artificial surface is at least 1.0 m² or
(ii) the artificial surface is a part of the extracorporeal circulation outside of the body of the subject or
(iii) the artificial surface is part of a dialysis equipment, such as the dialyzer membrane, tubing system, bubble-catcher and drip chambers (exposure of blood to air).

The present disclosure also provides a medical device coated with the antibody or antigen-binding fragment of the invention, wherein the device is a dialysis machine, an extracorporeal membrane oxygenation system for oxygenation of blood, a device for assisted pumping of blood, a blood dialysis device, a device for the extracorporeal filtration of blood, a repository for use in the collection of blood, an intraluminal catheter, a stent, and/or accessories for any one of said devices including tubing, cannulae, centrifugal pump, valve, port, and/or diverter.

The present disclosure also provides a method comprising administering the anti-FXII antibody or antigen binding fragment thereof to a patient receiving an extracorporeal procedure, wherein the medical procedure comprises contact with at least one of:
(a) Hemodialysis,
(b) Plasmapheresis,
(c) Lipidapheresis.

The present disclosure also provides a method for treating or preventing a condition associated with increased renal vascular permeability, including progressive nephrotic syndrome, protein-wasting diabetic nephropathy, wherein the method comprises administering the anti-FXII antibody or antigen binding fragment thereof.

KEY TO SEQUENCE LISTING

Figure 1A:
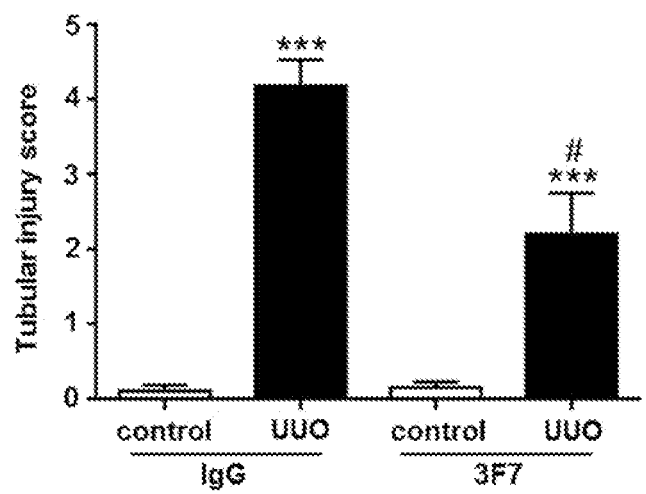
FIG. 1A is a representation of the tubular injury score determined in control and obstructed (UUO) kidneys from IgG- or 3F7-treated mice at day 10 post injury.

SEQ ID NO: 1 is an amino acid sequence of wild-type Infestin-4
SEQ ID NO: 2 is an amino acid sequence of wild-type SPINK-1
SEQ ID NO: 3 is an amino acid sequence of SPINK-1 mutant K1
SEQ ID NO: 4 is an amino acid sequence of SPINK-1 mutant K2
SEQ ID NO: 5 is an amino acid sequence of SPINK-1 mutant K3
SEQ ID NO: 6 is an amino acid sequence from the $V_H$ of anti-FXII antibody 3F7
SEQ ID NO: 7 is an amino acid sequence from the $V_L$ of anti-FXII antibody 3F7
SEQ ID NO: 8 is an amino acid sequence from a $V_H$ CDR1 of an anti-FXII antibody
SEQ ID NO: 9 is an amino acid sequence from a $V_H$ CDR2 of an anti-FXII antibody
SEQ ID NO: 10 is an amino acid sequence from a $V_H$ CDR2 of an anti-FXII antibody
SEQ ID NO: 11 is an amino acid sequence from a $V_H$ CDR3 of an anti-FXII antibody
SEQ ID NO: 12 is an amino acid sequence from a $V_H$ CDR3 of an anti-FXII antibody
SEQ ID NO: 13 is an amino acid sequence from a $V_L$ CDR1 of an anti-FXII antibody
SEQ ID NO: 14 is an amino acid sequence from a $V_L$ CDR2 of an anti-FXII antibody
SEQ ID NO: 15 is an amino acid sequence from a $V_L$ CDR3 of an anti-FXII antibody
SEQ ID NO: 16 is an amino acid sequence from a $V_L$ CDR3 of an anti-FXII antibody
SEQ ID NO: 17 is an amino acid sequence from a $V_L$ CDR1 of an anti-FXII antibody
SEQ ID NO: 18 is an amino acid sequence of the $V_H$ of anti-FXII antibody gVR115
SEQ ID NO: 19 is an amino acid sequence of the $V_L$ of anti-FXII antibody gVR115
SEQ ID NO: 20 is an amino acid sequence of the heavy chain of anti-FXII antibody gVR115
SEQ ID NO: 21 is an amino acid sequence of the light chain of anti-FXII antibody gVR115
SEQ ID NO: 22 is an amino acid sequence from a human Factor XII
SEQ ID NO: 23 is an amino acid sequence of a mature form of human albumin
SEQ ID NO: 24 is an amino acid sequence of an Infestin-4 variant
SEQ ID NO: 25 is an amino acid sequence of an Infestin-4 variant

DESCRIPTION

General

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or groups of compositions of matter.

Those skilled in the art will appreciate that the present disclosure is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features.

The present disclosure is not to be limited in scope by the specific examples described herein, which are intended for the purpose of exemplification only. Functionally-equivalent products, compositions and methods are clearly within the scope of the present disclosure.

Any example of the present disclosure herein shall be taken to apply mutatis mutandis to any other example of the disclosure unless specifically stated otherwise.

Unless specifically defined otherwise, all technical and scientific terms used herein shall be taken to have the same meaning as commonly understood by one of ordinary skill in the art (for example, in cell culture, molecular genetics, immunology, immunohistochemistry, protein chemistry, and biochemistry).

Unless otherwise indicated, the recombinant protein, cell culture, and immunological techniques utilized in the present disclosure are standard procedures, well known to those skilled in the art. Such techniques are described and explained throughout the literature in sources such as, J. Perbal, A Practical Guide to Molecular Cloning, John Wiley and Sons (1984), J. Sambrook et al. Molecular Cloning: A Laboratory Manual, Cold Spring Harbor Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbor Laboratory, (1988), and J. E. Coligan et al. (editors) Current Protocols in Immunology, John Wiley & Sons (including all updates until present).

The description and definitions of variable regions and parts thereof, immunoglobulins, antibodies and fragments thereof herein may be further clarified by the discussion in Kabat Sequences of Proteins of Immunological Interest, National Institutes of Health, Bethesda, Md., 1987 and 1991, Bork et al., J Mol. Biol. 242, 309-320, 1994, Chothia and Lesk J. Mol Biol. 196:901-917, 1987, Chothia et al. Nature 342, 877-883, 1989 and/or or Al-Lazikani et al., J Mol Biol 273, 927-948, 1997. Any discussion of a protein or antibody herein will be understood to include any variants of the protein or antibody produced during manufacturing and/or storage. For example, during manufacturing or storage an antibody can be deamidated (e.g., at an asparagine or a glutamate residue) and/or have altered glycosylation and/or have a glutamine residue converted to pyroglutamine and/or have a N-terminal or C-terminal residue removed or "clipped" and/or have part or all of a signal sequence incompletely processed and, as a consequence, remain at the terminus of the antibody. It is understood that a composition comprising a particular amino acid sequence may be a heterogeneous mixture of the stated or encoded sequence and/or variants of that stated or encoded sequence.

The term "and/or", e.g., "X and/or Y" shall be understood to mean either "X and Y" or "X or Y" and shall be taken to provide explicit support for both meanings or for either meaning.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

As used herein the term "derived from" shall be taken to indicate that a specified integer may be obtained from a particular source albeit not necessarily directly from that source.

Selected Definitions

The terms "renal" and "kidney" are used interchangeably herein.

Coagulation Factor XII, also known as Hageman factor or FXII, is a plasma protein. It is the zymogen form of Factor XIIa, an enzyme of the serine protease (or serine endopeptidase) class. In humans, Factor XII is encoded by the F12 gene. For the purposes of nomenclature only and not limitation exemplary sequences of human Factor XII is set out in NCBI Reference Sequence: NP_000496.2; in NCR protein accession number NP_000496 and in SEQ ID NO: 22. Additional sequences of Factor XII can be determined using sequences provided herein and/or in publically available databases and/or determined using standard techniques (e.g., as described in Ausubel et al., (editors), Current Protocols in Molecular Biology, Greene Pub. Associates and WileyInterscience (1988, including all updates until present) or Sambrook et al., Molecular Cloning: A Laboratory Manual, Cold Spring Harbor Laboratory Press (1989)).

As used herein, the term "Factor XII inhibitor" or "FXII inhibitor" or "inhibitor of FXII" refers to an inhibitor of either or both of Factor XII (prior to activation, i.e., its zymogen) and activated Factor XII (FXIIa) as well as to the activation of FXII. Thus, "inhibitor(s) of FXII" can include inhibitors of either or both of FXII and FXIIa (also termed αFXIIa) as well as the activation of FXII, including the FXIIa cleavage products FXIIa alpha and FXIIa beta (also termed FXIIf). FXII inhibitors encompass functional variants and fragments of the wild-type inhibitor. A functional variant or fragment is a molecule that retains at least 50% (e.g., about 50%, or about 60%, or about 70%, or about 80%, or about 90%, or about 95%, or about 99%, or about 100%) of the ability of the wild-type molecule to inhibit FXII, FXIIa or the activation of FXII. In one example, the FXII inhibitors are non-endogenous inhibitors; that is, they are not inhibitors that occur naturally in the human or animal body.

The term "direct FXII inhibitor" or "direct inhibitor", as used herein, refers to an inhibitor that acts via contact (e.g., binding) with FXII (or FXIIa), i.e., the FXII inhibitor binds to FXII and/or FXIIa and inhibits its activity and/or activation. In contrast, an indirect inhibitor may act without contacting FXII (or FXIIa) protein. For example, antisense RNA can be used to decrease expression of the FXII gene, or a small molecule can inhibit the effects of FXIIa via interactions with downstream FXIIa reaction partners like Factor XI; these do not interact directly with the FXII protein. Thus, an indirect inhibitor, in contrast to a direct inhibitor, acts upstream or downstream from the FXII protein. In one example, the FXII inhibitors are specific to FXII or FXIIa, in particular specific to human FXII or FXIIa.

As used herein, the term "inhibitor of Factor XII" or "Factor XII inhibitor" shall in addition be understood so as to not encompass C1-INH, i.e. "with the proviso that the inhibitor of Factor XII is not C1 INH".

As used herein, the term "binds" in reference to the interaction of a protein or an antigen binding site thereof with an antigen means that the interaction is dependent upon the presence of a particular structure (e.g., an antigenic determinant or epitope) on the antigen. For example, an antibody recognizes and binds to a specific protein structure rather than to proteins generally. If an antibody binds to epitope "A", the presence of a molecule containing epitope "A" (or free, unlabeled "A"), in a reaction containing labeled "A" and the protein, will reduce the amount of labeled "A" bound to the antibody.

As used herein, the term "specifically binds" or "binds specifically" shall be taken to mean that a protein or an antigen binding site thereof reacts or associates more frequently, more rapidly, with greater duration and/or with greater affinity with a particular antigen or cell expressing same than it does with alternative antigens or cells. For example, a protein or an antigen binding site thereof binds to FXII (or FXIIa) with materially greater affinity (e.g., 1.5 fold or 2 fold or 5 fold or 10 fold or 20 fold or 40 fold or 60 fold or 80 fold to 100 fold or 150 fold or 200 fold) than it does to other blood clotting factors or to antigens commonly recognized by polyreactive natural antibodies (i.e., by naturally occurring antibodies known to bind a variety of antigens naturally found in humans). Generally, but not necessarily, reference to binding means specific binding, and each term shall be understood to provide explicit support for the other term.

The term "amidolytic activity" refers to the ability of the inhibitor of FXII to catalyse the hydrolysis of at least one peptide bond in another polypeptide. The term "identity" or "identical" as used herein refers to the percentage number of amino acids that are identical or constitute conservative substitutions. Homology may be determined using sequence comparison programs such as GAP (Deveraux et al., 1984, Nucleic Acids Research 12, 387-395), which is incorporated herein by reference. In this way sequences of a similar or substantially different length to those cited herein could be compared by insertion of gaps into the alignment, such gaps being determined, for example, by the comparison algorithm used by GAP.

A "half-life enhancing polypeptide" or "HLEP" is a polypeptide fusion partner that may increase the half-life of the FXII inhibitor in vivo in a patient or in an animal. Examples include albumin and immunoglobulins and their fragments, such as Fc domains, or derivatives, which may be fused to a FXII inhibitor directly or via a cleavable or non-cleavable linker. Ballance et al. (WO 2001/79271) described fusion polypeptides comprising a multitude of different therapeutic polypeptides fused to human serum albumin. As used herein, the terms "albumin" and "serum albumin" encompass human albumin (HA) and variants thereof. For the purposes of nomenclature only and not limitation exemplary sequences of the full mature form of albumin is set out in SEQ ID NO: 23, as well as albumin from other species and variants thereof. As used herein, "albumin" refers to an albumin polypeptide or amino acid sequence, or an albumin variant, having one or more functional activities (e.g. biological activities) of albumin. In certain examples, albumin is used to stabilize or prolong the therapeutic activity of a FXII inhibitor. The albumin may be derived from any vertebrate, especially any mammal, for example human, monkey, cow, sheep, or pig. Non-mammalian albumin can also be used and includes, but is not limited to, albumin from chicken and salmon. The albumin portion of the albumin-linked polypeptide may be from a different animal than the therapeutic polypeptide portion. See WO 2008/098720 for examples of albumin fusion proteins, incorporated herein by reference in its entirety.

The term "recombinant" shall be understood to mean the product of artificial genetic recombination. Accordingly, in the context of a recombinant protein comprising an antibody variable region, this term does not encompass an antibody naturally-occurring within a subject's body that is the product of natural recombination that occurs during B cell maturation. However, if such an antibody is isolated, it is to be considered an isolated protein comprising an antibody variable region. Similarly, if nucleic acid encoding the protein is isolated and expressed using recombinant means, the resulting protein is a recombinant protein. A recombinant protein also encompasses a protein expressed by artificial recombinant means when it is within a cell, tissue or subject, e.g., in which it is expressed.

The term "protein" shall be taken to include a single polypeptide chain, i.e., a series of contiguous amino acids linked by peptide bonds or a series of polypeptide chains covalently or non-covalently linked to one another (i.e., a polypeptide complex). For example, the series of polypeptide chains can be covalently linked using a suitable chemical or a disulfide bond. Examples of non-covalent bonds include hydrogen bonds, ionic bonds, Van der Waals forces, and hydrophobic interactions.

The term "polypeptide" or "polypeptide chain" will be understood from the foregoing paragraph to mean a series of contiguous amino acids linked by peptide bonds.

The skilled artisan will be aware that an "antibody" is generally considered to be a protein that comprises a variable region made up of a plurality of polypeptide chains, e.g., a polypeptide comprising a light chain variable region ($V_L$) and a polypeptide comprising a heavy chain variable region ($V_H$). An antibody also generally comprises constant domains, some of which can be arranged into a constant region, which includes a constant fragment or fragment crystallizable (Fc), in the case of a heavy chain. A $V_H$ and a $V_L$ interact to form a Fv comprising an antigen binding region that is capable of specifically binding to one or a few closely related antigens. Generally, a light chain from mammals is either a κ light chain or a λ light chain and a heavy chain from mammals is α, δ, ε, γ, or μ. Antibodies can be of any type (e.g., IgG, IgE, IgM, IgD, IgA, and IgY), class (e.g., IgG1, IgG2, IgG3, IgG4, IgA1 and IgA2) or subclass. The term "antibody" also encompasses humanized antibodies, primatized antibodies, human antibodies, synhumanized antibodies and chimeric antibodies. An "anti-FXII antibody" includes antibodies that bind to and/or inhibit either or both of the zymogen of FXII and the activated protein (FXIIa), including the FXIIa alpha and FXIIa beta cleavage fragments. In some examples, the antibody binds specifically to FXIIa or the alpha or beta chain fragments of FXIIa.

The terms "full-length antibody", "intact antibody" or "whole antibody" are used interchangeably to refer to an antibody in its substantially intact form, as opposed to an antigen binding fragment of an antibody. Specifically, whole antibodies include those with heavy and light chains including an Fc region. The constant domains may be wild-type sequence constant domains (e.g., human wild-type sequence constant domains) or amino acid sequence variants thereof.

As used herein, "variable region" refers to the portions of the light and/or heavy chains of an antibody as defined herein that is capable of specifically binding to an antigen and includes amino acid sequences of complementarity determining regions (CDRs); i.e., CDR1, CDR2, and CDR3, and framework regions (FRs). Exemplary variable regions comprise three or four FRs (e.g., FR1, FR2, FR3 and optionally FR4) together with three CDRs. In the case of a protein derived from an IgNAR, the protein may lack a CDR2. $V_H$ refers to the variable region of the heavy chain. $V_L$ refers to the variable region of the light chain.

As used herein, the term "complementarity determining regions" (syn. CDRs; i.e., CDRI, CDR2, and CDR3) refers to the amino acid residues of an antibody variable domain, the presence of which are necessary for antigen binding. Each variable domain typically has three CDR regions identified as CDR1, CDR2 and CDR3. The amino acid positions assigned to CDRs and FRs can be defined according to Kabat *Sequences of Proteins of Immunological Interest*, National Institutes of Health, Bethesda, Md., 1987 and 1991 or other numbering systems in the performance of this disclosure, e.g., the canonical numbering system of Chothia and Lesk *J. Mol Biol.* 196: 901-917, 1987; Chothia et al. *Nature* 342, 877-883, 1989; and/or Al-Lazikani et al., *J Mol Biol* 273: 927-948, 1997; the IMGT numbering system of Lefranc et al., *Devel. And Compar. Immunol.*, 27: 55-77, 2003; or the AHO numbering system of Honnegher and Plükthun *J. Mol. Biol.*, 309:657-670, 2001.

"Framework regions" (FRs) are those variable domain residues other than the CDR residues.

As used herein, the term "variable region fragment" or "Fv" shall be taken to mean any protein, whether comprised of multiple polypeptides or a single polypeptide, comprising a $V_L$ and a $V_H$, wherein the $V_L$ and a $V_H$ are associated to form a complex having an antigen binding site, i.e., capable of specifically binding to an antigen. The $V_H$ and the $V_L$ which form the antigen binding site can be in a single polypeptide chain or in different polypeptide chains. Furthermore, an Fv of the disclosure (as well as any protein of the disclosure) may have multiple antigen binding sites which may or may not bind the same antigen. This term shall be understood to encompass fragments directly derived from an antibody as well as proteins corresponding to such a fragment produced using recombinant means. In some examples, the $V_H$ is not linked to a heavy chain constant domain ($C_H$) and/or the $V_L$ is not linked to a light chain constant domain ($C_L$). Exemplary Fv containing polypeptides or proteins include a Fab fragment, a Fab' fragment, a F(ab') fragment, a scFv, a diabody, a triabody, a tetrabody or higher order complex, or any of the foregoing linked to a constant region or domain thereof, e.g., $C_H2$ or $C_H3$ domain, e.g., a minibody or an antibody. A "Fab fragment" consists of a monovalent antigen-binding fragment of an antibody, and can be produced by digestion of a whole antibody with the enzyme papain, to yield a fragment consisting of an intact light chain and a portion of a heavy chain or can be produced using recombinant means. A "Fab' fragment" of an antibody can be obtained by treating a whole antibody with pepsin, followed by reduction, to yield a molecule consisting of an intact light chain and a portion of a heavy chain comprising a $V_H$ and a single constant domain. Two Fab' fragments are obtained per antibody treated in this manner. A Fab' fragment can also be produced by recombinant means. A "F(ab')2 fragment" of an antibody consists of a dimer of two Fab' fragments held together by two disulfide bonds, and is obtained by treating a whole antibody molecule with the enzyme pepsin, without subsequent reduction. A "Fab2" fragment is a recombinant fragment comprising two Fab fragments linked using, for example a leucine zipper or a $C_H3$ domain. A "single chain Fv" or "scFv" is a recombinant molecule containing the Fv of an antibody in which the variable region of the light chain and the variable region of the heavy chain are covalently linked by a suitable, flexible polypeptide linker. As will be apparent from the foregoing discussion, this term encompasses an antibody or an antigen binding fragment thereof comprising a $V_H$ and a $V_L$.

As used herein, the terms "sequence identity" or "identity" between two polypeptide sequences indicates the percentage of amino acids that are identical between the sequences, preferably over the entire length of the amino acid sequences as encoded by SEQ ID NO. 1, 2, 3, 4, 5, 6, 7, 8, 9, 10, 11, 12, 13, 14, 15, 16, 17, 18, 19, 20, 21, 24, 25. Preferred, polypeptide sequences of the invention have a sequence identity of respectively at least about 70%, 75%, 80%, 85%, 90%, 95%, 96%, 97%, 98%, or 99%.

As used herein, the terms "preventing", "prevent" or "prevention" include administering a compound of the disclosure to thereby stop or hinder the development or progression of at least one symptom of a condition.

As used herein, the terms "treating", "treat" or "treatment" include administering a protein described herein to thereby reduce or eliminate at least one symptom of a specified disease or condition or to slow progression of the disease or condition. As used herein, the term "subject" shall be taken to mean any animal including humans, for example a mammal. Exemplary subjects include but are not limited to humans and nonhuman primates. For example, the subject is a human.

Preventing and Treating Renal Fibrosis and Chronic Kidney Disease

The disclosure herein provides a method for treating renal fibrosis and/or chronic kidney disease (CKD) by administering to the subject an inhibitor of Factor XII.

The disclosure also provides, a method for preventing renal fibrosis and/or CKD in a subject comprising administering to the subject an inhibitor of Factor XII.

CKD is a progressive disease that can be subdivided in stages I through V. Depending on the severity of the disease, progression from one stage to another may be slowed down and/or prevented by administering to the subject an inhibitor of Factor XII.

The ways of treating and preventing disclosed herein apply to both native and transplant/allograft kidneys.

In one example, the subject suffers from one or more of the following renal disorders:
  Kidney Fibrosis
  Diabetic Nephropathy, Glomerulonephritides
  Lupus-Nephritis
  Renal Vasculis
  Gomerulosclerosis
  Hypertensive Nephropathy (nephrosclerosis)
  Interstitial Nephritis
  Autosomal dominant polycystic kidney disease
  Alport Syndrome
  Analgesic Nephropathy
  Kidney allograft injury related to ischemia reperfusion or rejection.

In one example, the subject has suffered or suffers from a condition associated with renal or kidney fibrosis. For example, the subject has suffered or suffers from diabetes.

The methods of the present disclosure can be readily applied to any form of renal disorder associated with renal fibrosis and/or CKD.

In one example, the subject is at risk of developing renal fibrosis and/or CKD, but the onset of renal fibrosis has not yet occurred. A subject is at risk if he or she has a higher risk of developing renal fibrosis and/or CKD than a control population. The control population may include one or more subjects selected at random from the general population (e.g., matched by age, gender, race and/or ethnicity) who have not suffered from or have a family history of diabetes or other kidney diseases associated with renal fibrosis.

A subject can be considered at risk for renal fibrosis and/or CKD if a "risk factor" associated with renal fibrosis and/or CKD is found to be associated with that subject (reduced GFR, proteinuria, diabetes, hypertension, obesity, presence of human leucocyte antibodies in kidney transplant patients). A risk factor can include any activity, trait, event or property associated with a given disorder, for example, through statistical or epidemiological studies on a population of subjects. A subject can thus be classified as being at risk for renal fibrosis even if studies identifying the underlying risk factors did not include the subject specifically.

As discussed above and in the examples section below, methods of the disclosure achieve one or more of the following effects:

Treatment with an inhibitor of FXIIa
(i) markedly reduces the abundance of extracellular matrix proteins,
(ii) neither affects macrophage accumulation nor cytokine production at an early and late stage,
(iii) leads to a marked reduction in the number of apoptotic renal tubular epithelial cells at an early and a late stage,
(iv) leads to an increase in the number of proliferating renal tubular epithelial cells (=regeneration) at an early and a late stage, and/or
(v) attenuates body weight loss.

As will be apparent to the skilled person a "reduction" or "attenuation" in a symptom or effect of a renal disorder such as renal fibrosis in a subject will be comparative to another subject who has also suffered from a renal disorder such as renal fibrosis but who has not received treatment with a method described herein or to the subject prior to treatment. This does not necessarily require a side-by-side comparison of two subjects. Rather population data can be relied upon. For example a population of subjects suffering from renal fibrosis who have not received treatment with a method described herein (optionally, a population of similar subjects to the treated subject, e.g., age, weight, diabetic status) are assessed and the mean values are compared to results of a subject or population of subjects treated with a method described herein.

Inhibitors of Factor XII

In one example, the inhibitor of FXII is a direct FXII inhibitor, such as a specific FXII inhibitor. For example, the specific FXII inhibitor inhibits plasmatic serine proteases or other endogenous proteins other than FXII and/or FXIIa less than or equal to about 25% if used in a molar ratio of 1:1. For example, the specific inhibitor of FXII/FXIIa inhibitor inhibits plasmatic serine proteases other than FXII and/or FXIIa less than or equal to about 25% when said inhibitor is used in a molar ratio of 1:1 of the respective plasmatic serine protease to said inhibitor. In one example, the FXII inhibitor inhibits plasmatic serine proteases other than FXII and/or FXIIa less than or equal to about 20%, or less than or equal to about 15%, or less than or equal to about 10%, or less than or equal to about 5%, or less than or equal to about 1% if used in a molar ratio of 1:1. For example, a specific FXII antibody inhibits the plasmatic serine protease FXIa by about 5%, wherein the molar ratio of FXIa to said antibody is 1:1 whereas the same FXII antibody inhibits FXIIa by at least about 80%, or at least about 90%.

In one example, one other plasmatic serine protease is inhibited by more than about 50% if used in a molar ratio of 1:1 of the respective plasmatic serine protease to the inhibitor. In another example of the disclosure, two other plasmatic serine proteases are inhibited by more than about 50% if used in a molar ratio of 1:1 of the respective plasmatic serine protease to the inhibitor.

Serine Protease Inhibitors

In one example, the inhibitor of FXII is a serine protease inhibitor. For example, the inhibitor of FXII comprises a sequence corresponding to Infestin-4 or variants thereof. In one example, the inhibitor of FXII comprises a sequence corresponding to SPINK-1 or variants thereof.

Infestin-4

In one example, the disclosure provides an inhibitor of FXII comprising infestin domain 4 (referred to as "Infestin-4"). Infestins are a class of serine protease inhibitors derived from the midgut of the hematophagous insect, *Triatoma infestans*, a major vector for the parasite *Trypanosoma cruzi*, known to cause Chagas disease. (Campos I T N et al. 32 Insect Biochem. Mol. Bio. 991-997, 2002; Campos I T N et al. 577 FEBS Lett. 512-516, 2004; WO 2008/098720.) This insect uses these inhibitors to prevent coagulation of ingested blood. The infestin gene encodes 4 domains that result in proteins that can inhibit different factors in the coagulation pathway. In particular, domain 4 encodes a protein (Infestin-4) that is a strong inhibitor of FXIIa. Infestin-4 has been administered in mice without resulting in bleeding complications (WO 2008/098720; Hagedorn et al., Circulation 2010; 121:1510-17.)

In one embodiment, the inhibitor of FXII comprises Infestin-4. The term "Infestin-4," as used herein, encompasses variants or fragments of the wild-type peptide that retain the ability to inhibit FXII. For the purposes of nomenclature only and not limitation an exemplary sequence of Infestin-4 is set out in SEQ ID NO: 1.

In one example, the Infestin-4 is chosen for its ability to inhibit FXIIa. In one example, the Infestin-4 comprises a variant of Infestin-4, wherein the variant comprises Infestin domain 4, and optionally, Infestin domains 1, 2, and/or 3. In one example, the Infestin-4 is a $(His)_6$-tagged Infestin-4 construct.

In another example, the Infestin-4 is a fusion protein comprising a fusion partner, such as a half-life enhancing polypeptide (e.g., albumin, an Fc domain of an IgG, or PEG), linked or bound to infestin-4. In one example, a linker connects the fusion partner to Infestin-4. In various embodiments, the Infestin-4 is the rHA-Infestin-4 protein described in Hagedorn et al., Circulation 2010; 117:1153-60. In one example, a composition comprises albumin bound to the rHA-Infestin-4 protein described in Hagedorn et al., Circulation 2010; 117:1153-60, by a flexible linker. In another example, other Infestin-4 inhibitors of FXII are used, examples of which are described in WO 2008/098720 and Hagedorn et al., Circulation 2010; 117:1153-60, both of which are incorporated by reference in their entirety.

In one example, the inhibitor of FXII is a variant of Infestin-4. As used here, the term "variant" of Infestin-4 refers to a polypeptide with one or more amino acid mutation, wherein "mutation" is defined as a substitution, a deletion, or an addition, to the wild type Infestin-4 sequence (SEQ ID NO: 1). The term "variant" of Infestin-4 also includes functional fragments of the wild type or a mutated Infestin-4 sequence.

In one example, the one or more mutations to the wild type Infestin-4 sequence do not substantially alter the functional ability of the polypeptide to inhibit FXII. For example, the one or more mutations do not completely or substantially remove the ability of the polypeptide to inhibit FXII. For example, the variant retains at least about 20%, or about 30%, or about 40%, or about 50%, or about 60%, or about 70%, or about 80%, or about 90%, or about 95%, or about 98%, or about 99%, or more of the inhibitory ability of wild type Infestin-4.

In one example, the inhibitor of FXII comprises an Infestin-4 variant comprising residues 2-13 from the amino terminal of the wild type Infestin-4 sequence as set forth in SEQ ID NO: 1. For example, the Infestin-4 variant comprises the amino acid sequence set forth in SEQ ID NO: 24.

In one example, the inhibitor of FXII comprises an Infestin-4 variant comprising residues 2-13 of SEQ ID NO:

1 and also comprising at least one amino acid mutations, as compared to the wild type Infestin-4 sequence (SEQ ID NO: 1), outside residues 2-13 of SEQ ID NO: 1. For example, the Infestin-4 variant comprises at least two amino acid mutations, or at least three amino acid mutations, or at least four amino acid mutations, or at least five amino acid mutations. For example, the inhibitor of FXII comprises a polypeptide sequence comprising SEQ ID NO: 1 modified to contain between 1 and 5 amino acid mutations outside of N-terminal amino acid positions 2-13 of SEQ ID NO: 1.

In one example, the inhibitor of FXII is an Infestin-4 variant which retains six conserved cysteine residues from the wild type Infestin-4 sequence. In one example, the six conserved cysteine residues are amino acids at positions 6, 8, 16, 27, 31, and 48 of the wild type Infestin-4 sequence (SEQ ID NO: 1). In one example, the Infestin-4 variant comprises the final conserved cysteine at position 48. In another example, the exact positions of the cysteine residues, and relative positions to each other, may change from positions 6, 8, 16, 27, 31, and 48 of the wild type Infestin-4 sequence due to insertions or deletions in the Infestin-4 variant sequence.

In one example, the Infestin-4 variant is at least about 70% identical to the wild type Infestin4 sequence. For example, the Infestin-4 has an identity of at least about 75%, at least about 80%, at least about 85%, at least about 90%, at least about 95%, at least about 98%, or at least about 99% to the wild type Infestin-4 sequence. For example, the inhibitor of FXII comprises a polypeptide sequence comprising a sequence at least 70% identical to SEQ ID NO: 1 and retaining six conserved cysteine residues from SEQ ID NO: 1.

In one example, the inhibitor of FXII is an Infestin-4 variant retains six conserved cysteine residues from the wild type Infestin-4 sequence and/or has a sequence of at least about 70% identical to the wild type Infestin-4 sequence.

In one example, the inhibitor of FXII is an Infestin-4 variant comprising SEQ ID NO: 1 modified to contain 1-5 amino acid mutations outside of N-terminal amino acid positions 2-13 of SEQ ID NO: 1; and a sequence at least 70% identical to SEQ ID NO: 1 and retaining six conserved cysteine residues from SEQ ID NO: 1.

EXAMPLES

Method

In order to assess the efficacy of the 3F7 antibody in the treatment of experimental renal fibrosis, the UUO model of renal damage and fibrosis was employed. In this model mice develop severe interstitial renal fibrosis within 7-10 days after ureter obstruction.

For the obstruction of the left ureter 2-month-old C57Bl/6 mice were anaesthetized with ketamine/xylazine (50 and 5 mg/kg, respectively; Ketavet from Pfizer, Germany and Rompun from Bayer, Germany). The left side was shaved and a midline incision over the left kidney was made. The left ureter was tied off twice with a suture until the endpoint and the incision was closed. During the operation the body temperature was maintained by placing the mice on a 37° C. heating pad. Mice were divided into two groups: unilateral ureter obstruction (UUO) mice either receiving vehicle (IgG, as isotype control, 1 mg per mouse, n=5) or anti-FXIIa antibody (3F7, 1 mg per mouse, n=10). 3F7 was applied from the first day after UUO on. The substances were injected intravenously in the tail vein immediately after ligation and then daily thereafter until the mice were sacrificed for analysis. The contralateral kidney served as control (Schaefer L., et al., J Pathol, 2002). Mice were sacrificed on day 3 or 10 following UUO. Plasma and kidneys were analyzed 3 or 10 days after left ureter obstruction.

Example 1—Reduced Number of Atrophic Tubules/Reduced Tubular Dilatation

Figure 1B:
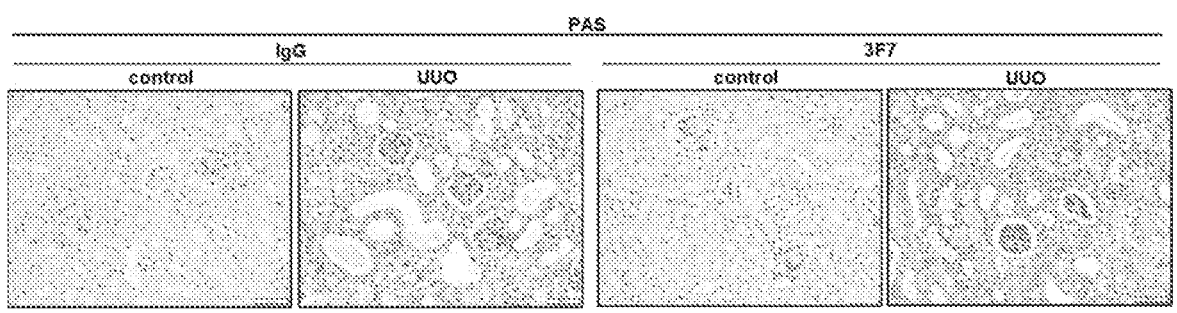
FIG. 1B shows PAS-stained sections from control and obstructed (UUO) kidneys from IgG- or 3F7-treated mice at day 10 post injury.

Mice were sacrificed 10 days after UUO as described in the method section above, and the extent of fibrosis was characterized by morphological and biochemical changes of the targeted organ. Serial sections (2 µm) of paraffin-embedded samples were stained with PAS. The severity of tubulointerstitial lesions was graded from 0 to 5 (normal, mild, moderate, advanced, or severe) using an activity index described previously (Moreth K., et al. J Clin Invest, 2010). For each animal at least 15 tubulointerstitial areas in the cortex and medulla were evaluated and graded for tubular dilatation and atrophy. Tubular injury scores for each mouse were calculated as the mean of the summed individual scores for each image. The results are represented in FIGS. 1A and 1B, wherein FIG. 1A represents the tubular injury score determined in the control and obstructed (UUO) kidneys from IgG- and 3F7-treated mice at day 10 post injury, and wherein FIG. 1B shows PAS-stained sections from control and obstructed (UUO) kidneys from IgG- and 3F7-treated mice at day 10 post injury. Treatment with the 3F7 antibody markedly reduced the number of atrophic tubules and reduced tubular dilatation in obstructed kidneys from mice treated with the 3F7 antibody vs. IgG treated controls, as can be seen from FIGS. 1A and 1B.

Example 2—Attenuating Effect on α-SMA Expression

Figure 2A:
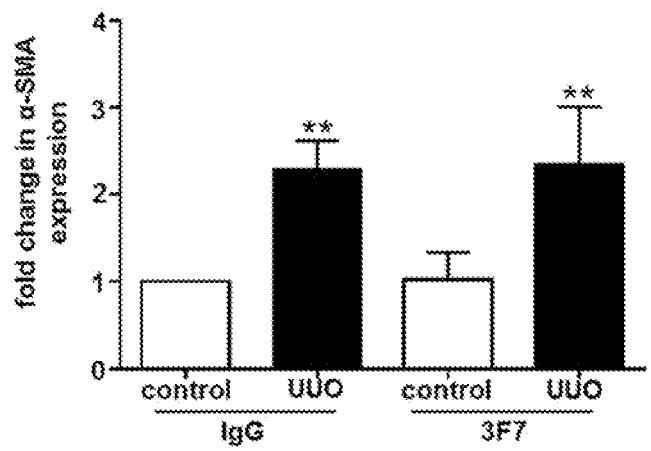
FIGS. 2A-C are representations of the expression of α-SMA as assessed by qPCR (FIG. 2A), western blotting (FIG. 2B) and immunohistochemistry (FIG. 2C), in control and obstructed (UUO) kidneys from IgG- or 3F7-treated mice at day 10 post injury.
Figure 2B:
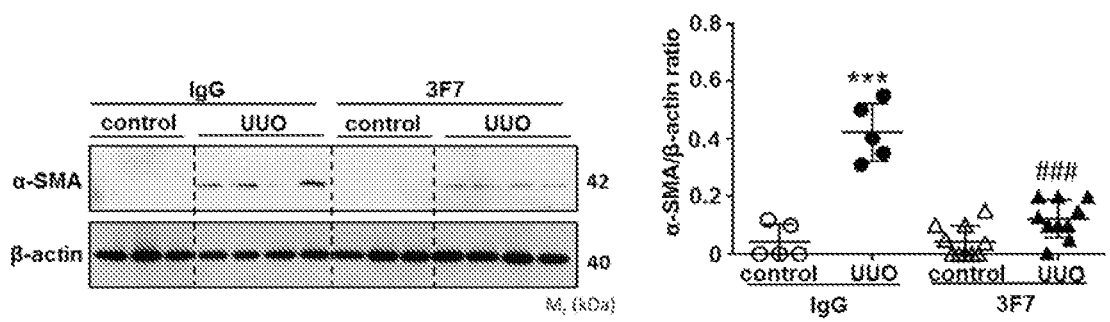
Figure 2C:
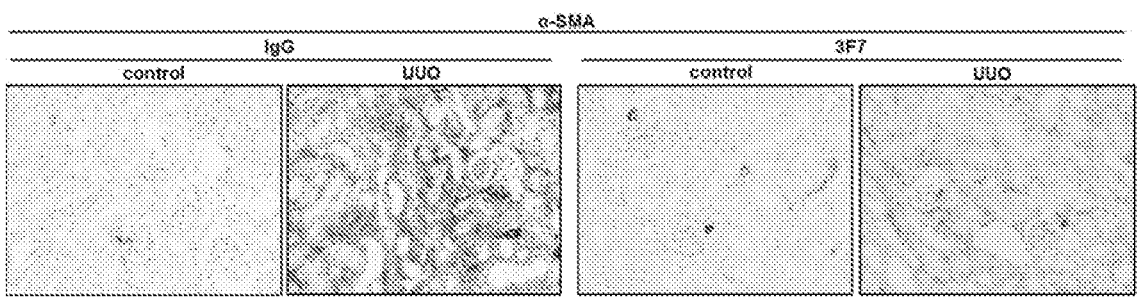

During UUO, isotype (IgG)-treated control kidneys showed a marked increase in the expression of α-SMA, as evaluated by qPCR, western blotting, and immunohistochemistry 10 days after UUO. Inhibition of FXIIa by the 3F7 antibody significantly reduced α-SMA expression in UUO kidneys, as can be seen from FIGS. 2B and C representing the expression of α-SMA as assessed by western blotting (FIG. 2B), and immunohistochemistry (FIG. 2C). There was no reduction of α-SMA mRNA expression, as assessed by qPCR, in UUO kidneys treated with the 3F7 antibody (FIG. 2A).

Example 3—Attenuating Effect on Expression of Extracellular Matrix Proteins

Figure 3A:
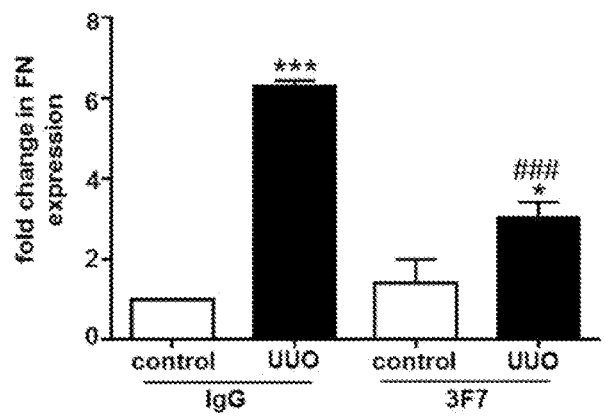
FIGS. 3A-C are representations of the expression of fibronectin as assessed by qPCR (FIG. 3A), western blotting (FIG. 3B) and immunohistochemistry (FIG. 3C), in control and obstructed (UUO) kidneys from IgG- or 3F7-treated mice at day 10 post injury.
Figure 3B:
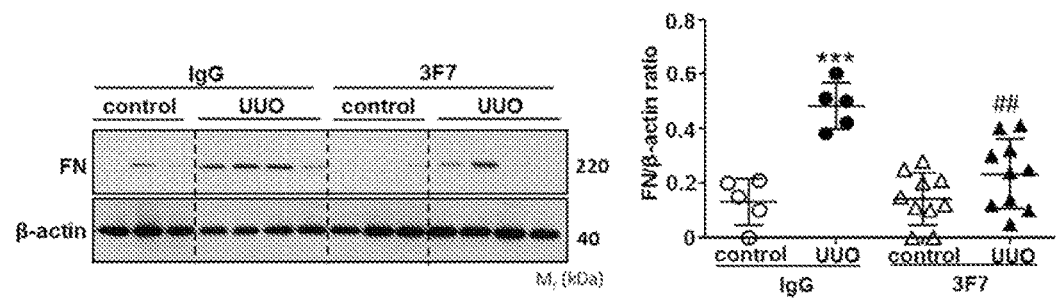
Figure 3C:
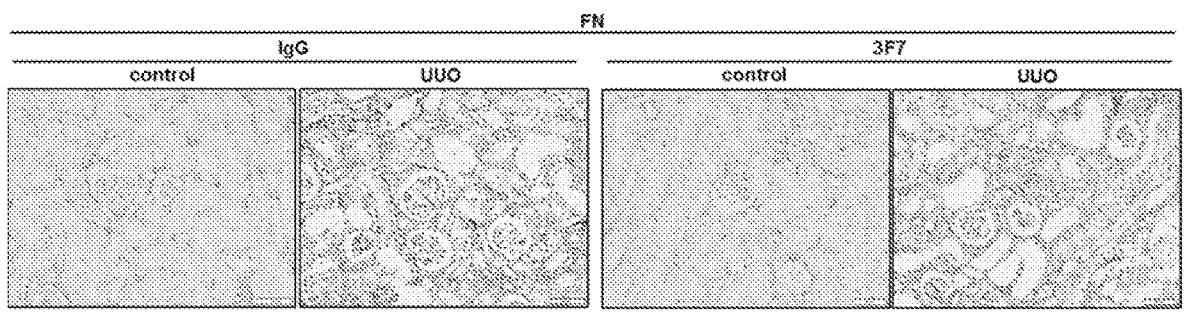
Figure 4A:
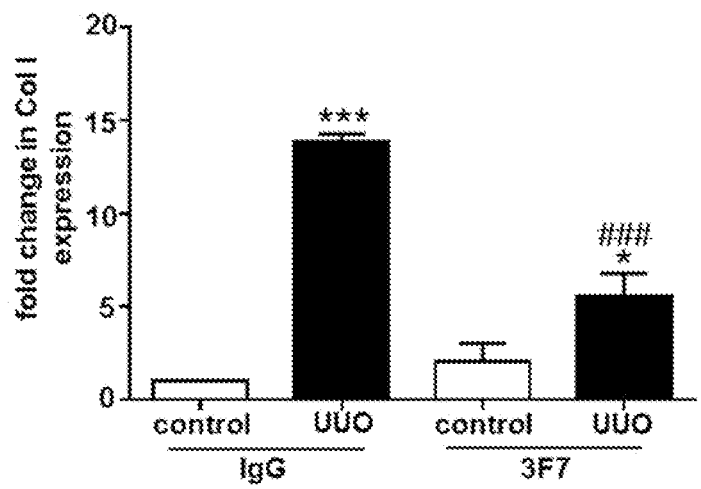
FIGS. 4A-C are representations of expression of collagen I (Col I) as assessed by qPCR (FIG. 4A), hydroxyproline content (FIG. 4B) and immunohistochemistry (FIG. 4C) in control and obstructed (UUO) kidneys from IgG- or 3F7-treated mice at day 10 post injury.
Figure 4B:
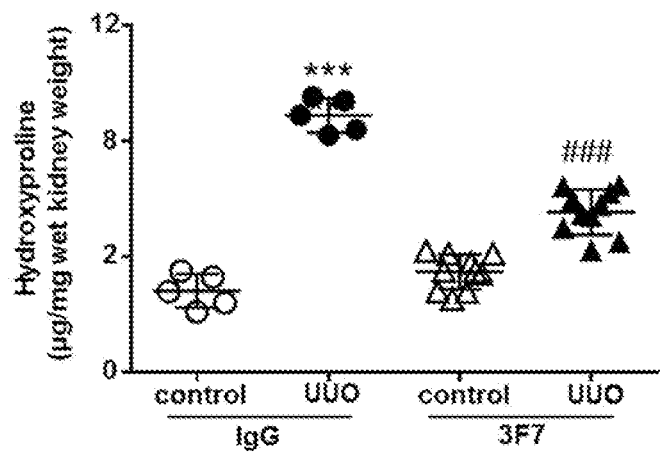
Figure 4C:
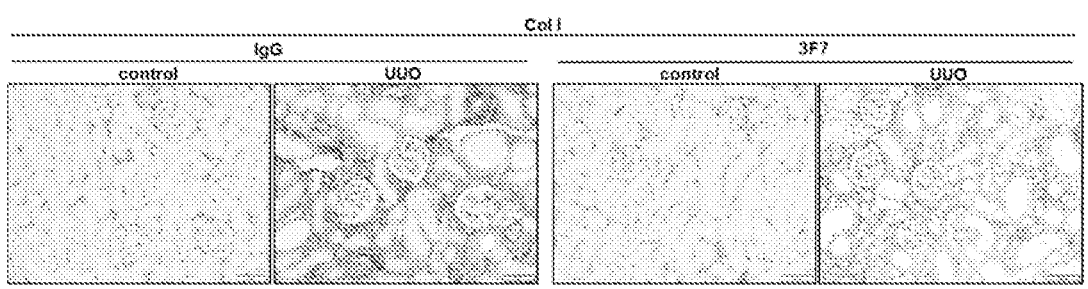

Similarly, UUO greatly augmented the expression of extracellular matrix proteins, fibronectin (FN) and collagen I (Col I), while treatment with the 3F7 antibody markedly reduced the abundance of these components in obstructed kidneys 10 days after UUO, as can be seen from FIGS. 3A-C representing the expression of FN as assessed by qPCR (FIG. 3A), western blotting (FIG. 3B), and immunohistochemistry (FIG. 3C), and FIGS. 4A-C representing the expression of Col I as assessed by qPCR (FIG. 4A), measurement of hydroxyproline content (FIG. 4B), and immunohistochemistry (FIG. 4C).

Example 4—Investigation Regarding Effect on F4/80-Positive Macrophages

Figure 5A:
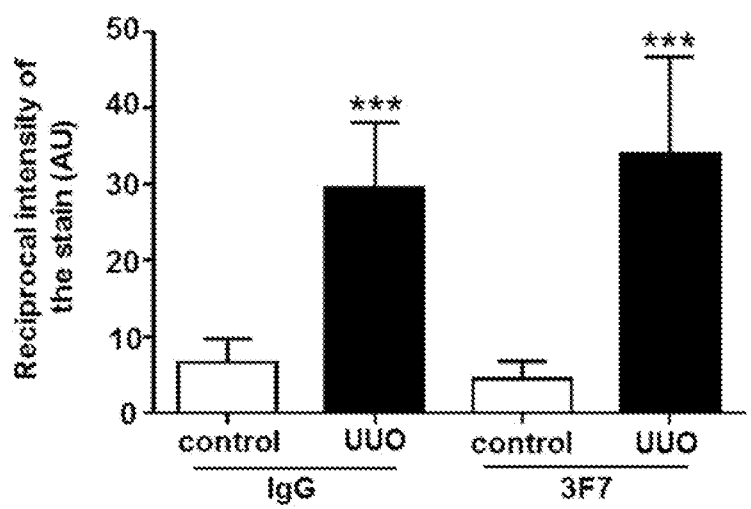
FIGS. 5A and 5B are representations of the accumulation of macrophages (F4/80 positive cells) in control and obstructed (UUO) kidneys from IgG- or 3F7-treated mice at day 10 post injury.
Figure 5B:
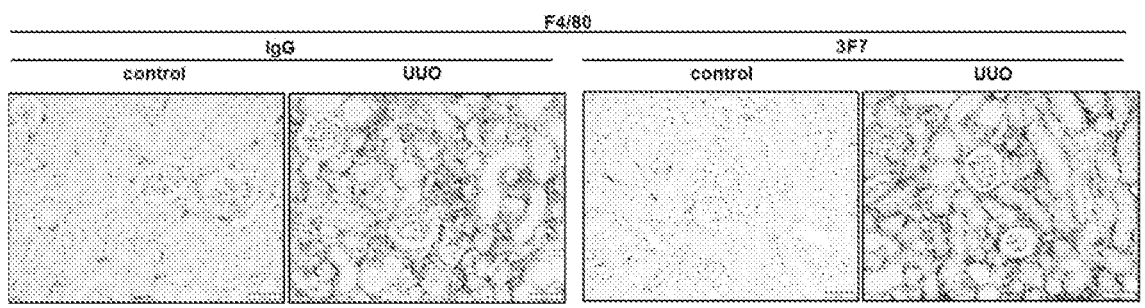

To determine whether the observed beneficial effects of FXIIa inhibition are the consequence of the suppression of inflammation, inventors also examined macrophage infiltration and cytokine levels in UUO kidneys 10 days after UUO. Inventors found that UUO induced accumulation of F4/80-positive macrophages in kidneys, whereas treatment with the 3F7 antibody had no impact on their numbers in obstructed organs. This result is represented in FIGS. 5A and 5B. Furthermore, there was no difference in the levels of TNF-α and IL-6 between IgG- and 3F7-treated UUO animals (data not shown).

Example 5—Reduction in the Number of Apoptotic Cells

Figure 6:
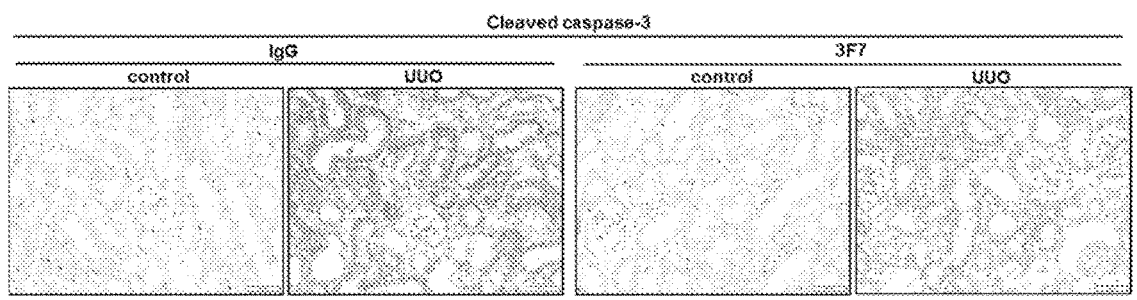
FIG. 6 shows representative cleaved caspase-3-stained sections from control and obstructed (UUO) kidneys from IgG- or 3F7-treated mice at day 3 post injury.

As 10 days after UUO fibrotic rather than inflammatory reactions take place, inventors also analyzed obstructed kidneys 3 days post injury. Surprisingly, administration of the 3F7 antibody neither affected macrophage accumulation nor cytokine production in UUO kidneys (data not shown). However, at this time point a marked reduction in the number of apoptotic (cleaved caspase-3 positive) renal tubular epithelial cells in 3F7-treated UUO mice as compared to IgG-challenged UUO littermates was observed, as can be seen from representative caspase-3-stained sections from control and obstructed (UUO) kidneys from IgG- or 3F7-treated mice at day 3 post injury shown in FIG. 6.

Figure 7:
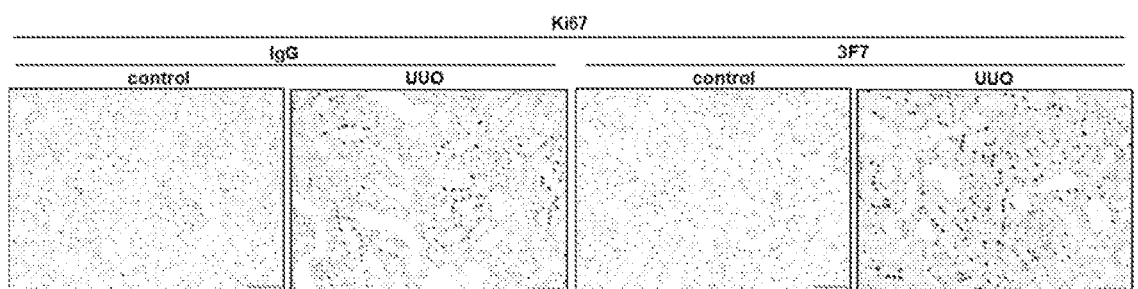
FIG. 7 shows representative Ki67-stained sections from control and obstructed (UUO) kidneys from IgG- or 3F7-treated mice at day 3 post injury.

Moreover, an increase in the number of proliferating (Ki67 positive) renal tubular epithelial cells in animals receiving 3F7 as compared to mice injected with IgG was seen, as can be seen from representative Ki67-stained sections from control and obstructed (UUO) kidneys from IgG- or 3F7-treated mice at day 3 post injury shown in FIG. 7.

Figure 8:
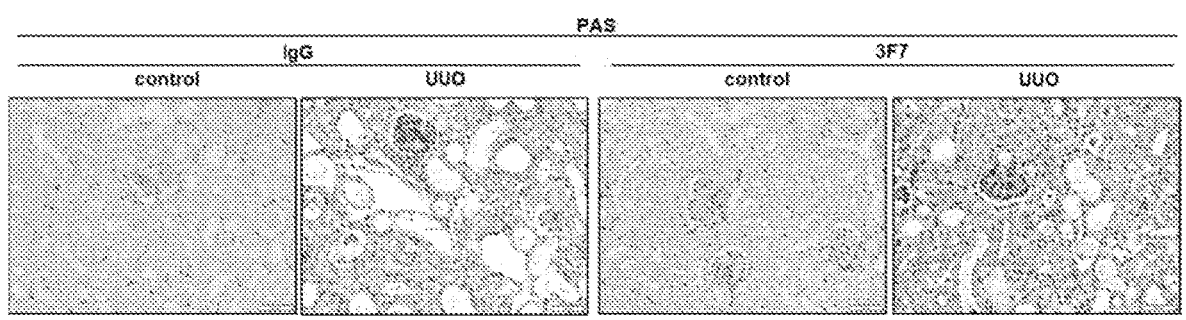
FIG. 8 shows representative PAS-stained sections from control and obstructed kidneys from IgG- or 3F7-treated mice at day 3 post injury.

This resulted in increased number of functional tubules and marked reduction of collapsed and atrophic tubules, as can be seen from representative PAS-stained sections from control and obstructed kidneys from IgG- or 3F7-treated mice at day 3 post injury shown in FIG. 8. Improved tubular morphology correlated very well with reduced accumulation of extracellular matrix components (data not shown).

These findings are quite surprising, because they differ from results observed in the bleomycin model of pulmonary fibrosis, where the number of apoptotic and proliferating alveolar epithelial cells at an early stage of lung injury was not different between 3F7- and IgG-treated mice.

Example 6—Attenuation of Body-Weight Loss

Figure 9:
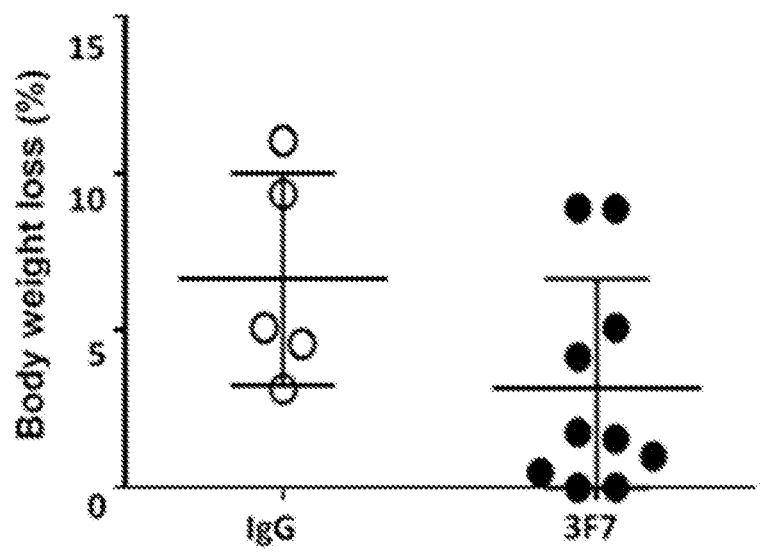
FIG. 9 represents the body weight loss of IgG- and 3F7-treated mice with control and obstructed (UUO) kidneys at day 10 post injury.
Figure 10:
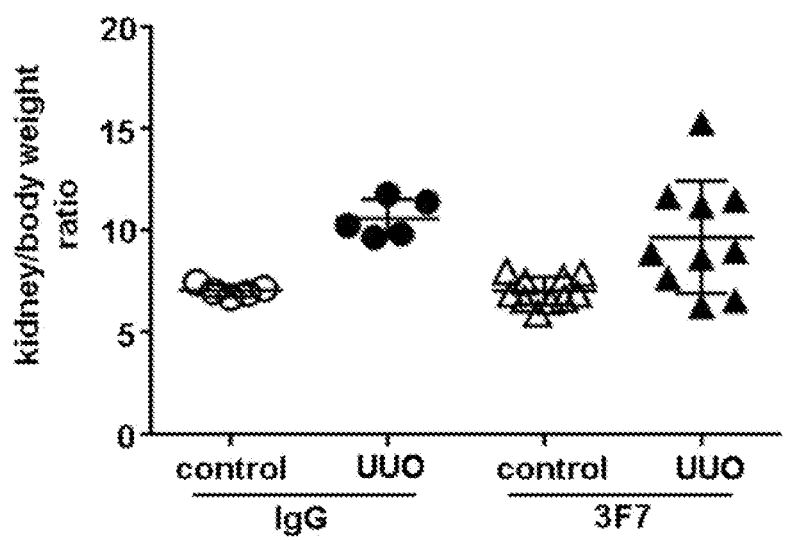
FIG. 10 represents the ratio of kidney/body weight of IgG- and 3F7-treated mice with control and obstructed (UUO) kidneys at day 10 post injury.

As can be seen from FIG. 9, the body weight loss following UUO is reduced in 3F7-treated mice as compared to IgG-treated mice. The same can be said for the kidney/body weight ratio as can be seen from FIG. 10.

Taken together, the examples show that inhibition of FXIIa in the UUO model of kidney fibrosis prevents the loss of functional tubules, reduces the evolution of renal fibrosis, and attenuates body-weight loss.

Example 7—Effect of 3F7 on Gene Expression

Gene Expression Profiling
Method

Purified total RNA was amplified and Cy3-labeled using the LIRAK kit (Agilent) following the kit instructions. Per reaction, 200 ng of total RNA was used. The Cy-labeled aRNA was hybridized overnight to 8×60K 60 mer oligonucleotide spotted microarray slides (Agilent Technologies, design ID 074809). Hybridization and subsequent washing and drying of the slides was performed following the Agilent hybridization protocol. The dried slides were scanned at 2 µm/pixel resolution using the InnoScan 900 (Innopsys, Carbonne, France). Image analysis was performed with Mapix 6.5.0 software, and calculated values for all spots were saved as GenePix results files. Stored data were evaluated using the R software and the limma package from BioConductor. Log mean spot signals were taken for further analysis. Data was background corrected using the Norm-Exp procedure on the negative control spots and quantile-normalized before averaging. Genes were ranked for differential expression using a moderated t-statistic. Pathway analyses were done using gene set tests on the ranks of the t-values.

Experiment and Results

To determine the effect of the anti-FXII antibody (3F7) treatment on the molecular signature in situ, the inventors performed gene expression profiling on UUO kidney homogenate samples from animals treated with either the anti-FXII antibody (3F7) or the IgG isotype control. The five most downregulated genes in the anti-FXII antibody treated group pointed towards suppressed: 1) apoptosis: harakiri (Hrk), 2) Wnt/β-catenin signalling: dickkopf-related protein 2 (Dkk2), 3) cell growth: nuclear receptor subfamily 2 group E member 1 (Nr2e1), CWF19 like cell cycle control factor 1 (Cwf19l1), and 4) glutamate transport: solute carrier family 1 member 3 (Slc1a3). The four most upregulated genes in the anti-FXII antibody treated group suggested an impact of the FXII inhibition on: 1) ECM-cell and cell-cell communication: desmoglein 1 gamma (Dsg1c), 2) angiogenesis: angiopoietin like 7 (Angptl7), 3) ion homeostasis: anoctamin 2 (Ano2), and 4) transcriptional regulation: regulatory factor X6 (Rfx6) (Table 1)

TABLE 1

Coding genes regulated in the kidney homogenates upon treatment with the anti-FXII antibody:

| GENE SYMBOL | GENE NAME | mean log 2 (fold-change) ± the half width of the 95% confidence interval | -log 10 (P-value) |
|---|---|---|---|
| Cwf19l1 | CWF19 like cell cycle control factor 1 | −1.53 ± 0.66 | 3.27 |
| Hrk | harakiri, BCL2 interacting protein | −1.26 ± 0.63 | 2.82 |
| Slc1a3 | solute carrier family 1 member 3 | −1.00 ± 0.47 | 3.00 |
| Nr2e1 | nuclear receptor subfamily 2 group E member 1 | −0.98 ± 0.48 | 2.89 |
| Dkk2 | dickkopf homolog 2 | −0.90 ± 0.44 | 2.86 |
| Dsg1c | desmoglein 1 gamma | 1.54 ± 0.76 | 2.87 |
| Ano2 | anoctamin 2 | 1.34 ± 0.64 | 2.86 |
| Angptl7 | angiopoietin-like 7 | 1.26 ± 0.62 | 2.86 |
| Rfx6 | regulatory factor X, 6 | 1.08 ± 0.44 | 3.42 |

Without wanting to be bound by any particular theory of action, the experimental results reported herein indicate that 3F7-treatment has effects on gene expression which may explain the reported effects in the experimental animals, for instance the reduction in the number of apoptotic cells (cf. example 5 above), or the aforementioned prevention of loss of functional tubules, reduced evolution of renal fibrosis, and attenuated body-weight loss.

The invention claimed is:

1. A method for treating chronic kidney disease and/or renal fibrosis in a subject in need thereof, comprising administering an effective amount of an inhibitor of Factor XII (FXII) to the subject,
wherein the subject is a human or animal;
wherein the inhibitor of FXII comprises an anti-FXII antibody, or an antigen-binding fragment thereof, comprising:
a $V_H$ comprising:
a CDR1 comprising the sequence set forth in SEQ ID NO: 8, a CDR2 comprising the sequence set forth in SEQ ID NO: 10, and a CDR3 comprising the sequence set forth in SEQ ID NO:12; or
a CDR1 comprising the sequence set forth in SEQ ID NO: 8, a CDR2 comprising the sequence set forth in SEQ ID NO: 9, and a CDR3 comprising the sequence set forth in SEQ ID NO: 11; and
a $V_L$ comprising:
a CDR1 comprising the sequence set forth in SEQ ID NO: 13, a CDR2 comprising the sequence set forth in SEQ ID NO: 14, and a CDR3 comprising the sequence set forth in SEQ ID NO: 16: or
a CDR1 comprising the sequence set forth in SEQ ID NO: 13, a CDR2 comprising the sequence set forth in SEQ ID NO: 14, and a CDR3 comprising the sequence set forth in SEQ ID NO: 15; and
wherein the chronic kidney disease and/or renal fibrosis is Nephritides, Lupus-Nephritis, C3-Glomerulonephritis, Dense Deposit Disease, atypical haemolytic-uremic syndrome, post-streptococcal glomerulonephritis, Henoch-Schoenlein Purpura, or antibody-mediated rejection of a kidney transplant.

2. The method according to claim 1, wherein the chronic kidney disease and/or renal fibrosis is a result of and/or is associated with one or more of the following: glomerulosclerosis, renal scarring, ischemia/reperfusion injury in kidneys, acute kidney injury, rejection of a kidney transplant/allograft, a recurrent underlying disease, and/or an inflammatory kidney disease related to FXII/FXIIa-mediated complement formation.

3. The method according to claim 1, wherein the inhibitor of FXII:
(i) binds to FXII and/or FXIIa; or
(ii) binds to FXII and/or FXIIa and inhibits the activity of FXII, inhibits the activity of FXIIa, and/or inhibits the activation of FXII.

4. The method according to claim 1, wherein the inhibitor of FXII is a protein comprising a variable region fragment (Fv).

5. The method according to claim 1, wherein the anti-FXII antibody comprises:
(i) a $V_H$ comprising the sequence set forth in SEQ ID NO: 6;
(ii) a $V_L$ comprising the sequence set forth in SEQ ID NO: 7.

6. The method according to claim 1, wherein the anti-FXII antibody comprises:
(i) a $V_H$ comprising the sequence set forth in SEQ ID NO: 18 and a $V_L$ comprising the sequence set forth in SEQ ID NO: 19; or
(ii) a heavy chain comprising the sequence set forth in SEQ ID NO: 20 and a light chain comprising the sequence set forth in SEQ ID NO: 21.

7. The method according to claim 1, wherein the anti-FXII antibody is a monospecific, bispecific, or trispecific IgG antibody.

8. The method according to claim 1, wherein the inhibitor of FXII is linked to a fusion partner that is polyethylene glycol (PEG) or a half-life enhancing polypeptide.

9. The method according to claim 8, wherein the half-life enhancing polypeptide is linked to the inhibitor of FXII via a linker.

10. The method according to claim 8, wherein the inhibitor of FXII is a fusion protein comprising human albumin linked to an inhibitor of FXII via a linker peptide.

11. The method according to claim 1, wherein the inhibitor of FXII is administered to the subject intravenously, subcutaneously, or intrathecally.

12. The method according to claim 1, wherein the inhibitor of FXII is administered to the subject in a single dose.

13. The method according to claim 1, wherein the inhibitor of FXII is administered to the subject at a concentration ranging from about 0.01 to about 100 mg/kg body weight.

14. The method according to claim 1, wherein the subject is at risk of developing a chronic kidney disease and/or renal fibrosis, wherein the chronic kidney disease and/or renal fibrosis is a result of and/or is associated with one or more of the following: glomerulosclerosis, renal scarring, ischemia/reperfusion injury in kidneys, acute kidney injury, rejection of a kidney transplant/allograft, a recurrent underlying disease, and/or an inflammatory kidney disease related to FXII/FXIIa-mediated complement formation.

15. The method according to claim 8, wherein the half-life enhancing polypeptide is selected from the group consisting of albumin, afamin, alpha fetoprotein, vitamin D binding protein, immunoglobulins, fragments of immunoglobulins, or derivatives of immunoglobulins.

16. The method according to claim 1, wherein the inhibitor of FXII is administered to the subject in a plurality of doses.

17. The method according to claim 13, wherein the inhibitor of FXII is administered to the subject at a concentration ranging from about 1 to about 20 mg/kg body weight.

* * * * *

SEQUENCE LISTING

```
<160> NUMBER OF SEQ ID NOS: 25

<210> SEQ ID NO 1
<211> LENGTH: 48
<212> TYPE: PRT
<213> ORGANISM: Artificial Sequence
<220> FEATURE:
<223> OTHER INFORMATION: amino acid sequence of wild-type Infestin-4

<400> SEQUENCE: 1

Glu Val Arg Asn Pro Cys Ala Cys Phe Arg Asn Tyr Val Pro Val Cys
1               5                   10                  15

Gly Ser Asp Gly Lys Thr Tyr Gly Asn Pro Cys Met Leu Asn Cys Ala
            20                  25                  30

Ala Gln Thr Lys Val Pro Gly Leu Lys Leu Val His Glu Gly Arg Cys
        35                  40                  45

<210> SEQ ID NO 2
<211> LENGTH: 56
<212> TYPE: PRT
<213> ORGANISM: Artificial Sequence
<220> FEATURE:
<223> OTHER INFORMATION: amino acid sequence of wild-type SPINK-1

<400> SEQUENCE: 2

Asp Ser Leu Gly Arg Glu Ala Lys Cys Tyr Asn Glu Leu Asn Gly Cys
1               5                   10                  15

Thr Lys Ile Tyr Asp Pro Val Cys Gly Thr Asp Gly Asn Thr Tyr Pro
            20                  25                  30

Asn Glu Cys Val Leu Cys Phe Glu Asn Arg Lys Arg Gln Thr Ser Ile
        35                  40                  45

Leu Ile Gln Lys Ser Gly Pro Cys
    50                  55

<210> SEQ ID NO 3
<211> LENGTH: 53
<212> TYPE: PRT
<213> ORGANISM: Artificial Sequence
<220> FEATURE:
<223> OTHER INFORMATION: SPINK-1 mutant K1

<400> SEQUENCE: 3

Asp Ser Leu Gly Arg Glu Val Arg Asn Pro Cys Ala Cys Phe Arg Asn
1               5                   10                  15

Tyr Val Pro Val Cys Gly Thr Asp Gly Asn Thr Tyr Pro Asn Glu Cys
            20                  25                  30

Val Leu Cys Phe Glu Asn Arg Lys Arg Gln Thr Ser Ile Leu Ile Gln
        35                  40                  45

Lys Ser Gly Pro Cys
    50

<210> SEQ ID NO 4
<211> LENGTH: 53
<212> TYPE: PRT
<213> ORGANISM: Artificial Sequence
<220> FEATURE:
<223> OTHER INFORMATION: SPINK-1 mutant K2
```

```
<400> SEQUENCE: 4

Asp Ser Leu Gly Arg Glu Val Arg Asn Pro Cys Ala Cys Phe Arg Asn
1               5                   10                  15

Tyr Val Pro Val Cys Gly Thr Asp Gly Asn Thr Tyr Gly Asn Glu Cys
                20                  25                  30

Met Leu Cys Ala Glu Asn Arg Lys Arg Gln Thr Ser Ile Leu Ile Gln
            35                  40                  45

Lys Glu Gly Pro Cys
        50

<210> SEQ ID NO 5
<211> LENGTH: 54
<212> TYPE: PRT
<213> ORGANISM: Artificial Sequence
<220> FEATURE:
<223> OTHER INFORMATION: SPINK-1 mutant K3

<400> SEQUENCE: 5

Asp Ser Leu Gly Arg Glu Val Arg Asn Pro Cys Ala Cys Phe Arg Asn
1               5                   10                  15

Tyr Val Pro Val Cys Gly Thr Asp Gly Asn Thr Tyr Gly Asn Glu Cys
                20                  25                  30

Met Leu Asn Cys Ala Glu Asn Arg Lys Arg Gln Thr Ser Ile Leu Ile
            35                  40                  45

Gln Lys Glu Gly Pro Cys
        50

<210> SEQ ID NO 6
<211> LENGTH: 129
<212> TYPE: PRT
<213> ORGANISM: Artificial Sequence
<220> FEATURE:
<223> OTHER INFORMATION: amino acid sequence from a VH of an anti-FXII
      antibody

<400> SEQUENCE: 6

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
                20                  25                  30

Ile Met Gln Trp Val Arg Gln Ala Pro Gly Lys Gly Leu Glu Trp Val
            35                  40                  45

Ser Gly Ile Arg Pro Ser Gly Gly Thr Thr Val Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Leu Pro Arg Ser Gly Tyr Leu Ile Ser Pro His Tyr Tyr
            100                 105                 110

Tyr Tyr Ala Leu Asp Val Trp Gly Gln Gly Thr Thr Val Thr Val Ser
        115                 120                 125

Ser

<210> SEQ ID NO 7
<211> LENGTH: 110
<212> TYPE: PRT
<213> ORGANISM: Artificial Sequence
<220> FEATURE:
```

<223> OTHER INFORMATION: amino acid sequence from a VL of an anti-FXII
      antibody

<400> SEQUENCE: 7

Gln Ser Glu Leu Thr Gln Pro Pro Ser Ala Ser Gly Thr Pro Gly Gln
1               5                   10                  15

Arg Val Thr Ile Ser Cys Ser Gly Ser Ser Asn Ile Gly Arg Asn
            20                  25                  30

Tyr Val Tyr Trp Tyr Gln Gln Val Pro Gly Thr Ala Pro Lys Leu Leu
            35                  40                  45

Ile Tyr Ser Asn Asn Gln Arg Pro Ser Gly Val Pro Asp Arg Phe Ser
        50                  55                  60

Gly Ser Lys Ser Gly Thr Ser Ala Ser Leu Val Ile Ser Gly Leu Arg
65                  70                  75                  80

Ser Glu Asp Glu Ala Asp Tyr Tyr Cys Ala Ala Trp Asp Ala Ser Leu
                85                  90                  95

Arg Gly Val Phe Gly Gly Gly Thr Lys Leu Thr Val Leu Gly
            100                 105                 110

<210> SEQ ID NO 8
<211> LENGTH: 5
<212> TYPE: PRT
<213> ORGANISM: Artificial Sequence
<220> FEATURE:
<223> OTHER INFORMATION: amino acid sequence from a VH CDR1 of an
      anti-FXII antibody

<400> SEQUENCE: 8

Lys Tyr Ile Met Gln
1               5

<210> SEQ ID NO 9
<211> LENGTH: 17
<212> TYPE: PRT
<213> ORGANISM: Artificial Sequence
<220> FEATURE:
<223> OTHER INFORMATION: amino acid sequence from a VH CDR2 of an
      anti-FXII antibody

<400> SEQUENCE: 9

Gly Ile Arg Pro Ser Gly Gly Thr Thr Val Tyr Ala Asp Ser Val Lys
1               5                   10                  15

Gly

<210> SEQ ID NO 10
<211> LENGTH: 17
<212> TYPE: PRT
<213> ORGANISM: Artificial Sequence
<220> FEATURE:
<223> OTHER INFORMATION: amino acid sequence from a VH CDR2 of an
      anti-FXII antibody
<220> FEATURE:
<221> NAME/KEY: X
<222> LOCATION: (3)..(3)
<223> OTHER INFORMATION: R or N or D
<220> FEATURE:
<221> NAME/KEY: X
<222> LOCATION: (4)..(4)
<223> OTHER INFORMATION: P or V or I or M
<220> FEATURE:
<221> NAME/KEY: X
<222> LOCATION: (5)..(5)
<223> OTHER INFORMATION: S or P or A
<220> FEATURE:
<221> NAME/KEY: X
<222> LOCATION: (6)..(6)

```
<223> OTHER INFORMATION: G or L or V or T
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: X
<222> LOCATION: (8)..(8)
<223> OTHER INFORMATION: G or S

<400> SEQUENCE: 10

Gly Ile Xaa Xaa Xaa Xaa Xaa Xaa Thr Val Tyr Ala Asp Ser Val Lys
1               5                   10                  15

Gly

<210> SEQ ID NO 11
<211> LENGTH: 20
<212> TYPE: PRT
<213> ORGANISM: Artificial Sequence
<220> FEATURE:
<223> OTHER INFORMATION: amino acid sequence from a VH CDR3 of an
      anti-FXII antibody

<400> SEQUENCE: 11

Ala Leu Pro Arg Ser Gly Tyr Leu Ile Ser Pro His Tyr Tyr Tyr
1               5                   10                  15

Ala Leu Asp Val
            20

<210> SEQ ID NO 12
<211> LENGTH: 20
<212> TYPE: PRT
<213> ORGANISM: Artificial Sequence
<220> FEATURE:
<223> OTHER INFORMATION: amino acid sequence from a VH CDR3 of an
      anti-FXII antibody
<220> FEATURE:
<221> NAME/KEY: X
<222> LOCATION: (9)..(9)
<223> OTHER INFORMATION: I or M or V
<220> FEATURE:
<221> NAME/KEY: X
<222> LOCATION: (10)..(10)
<223> OTHER INFORMATION: S or K
<220> FEATURE:
<221> NAME/KEY: X
<222> LOCATION: (11)..(11)
<223> OTHER INFORMATION: P or K or T or H
<220> FEATURE:
<221> NAME/KEY: X
<222> LOCATION: (12)..(12)
<223> OTHER INFORMATION: H or N or G or Q

<400> SEQUENCE: 12

Ala Leu Pro Arg Ser Gly Tyr Leu Xaa Xaa Xaa Xaa Tyr Tyr Tyr
1               5                   10                  15

Ala Leu Asp Val
            20

<210> SEQ ID NO 13
<211> LENGTH: 13
<212> TYPE: PRT
<213> ORGANISM: Artificial Sequence
<220> FEATURE:
<223> OTHER INFORMATION: amino acid sequence from a VL CDR1 of an
      anti-FXII antibody

<400> SEQUENCE: 13

Ser Gly Ser Ser Ser Asn Ile Gly Arg Asn Tyr Val Tyr
```

```
<210> SEQ ID NO 14
<211> LENGTH: 7
<212> TYPE: PRT
<213> ORGANISM: Artificial Sequence
<220> FEATURE:
<223> OTHER INFORMATION: amino acid sequence from a VL CDR2 of an
      anti-FXII antibody

<400> SEQUENCE: 14

Ser Asn Asn Gln Arg Pro Ser
1               5

<210> SEQ ID NO 15
<211> LENGTH: 10
<212> TYPE: PRT
<213> ORGANISM: Artificial Sequence
<220> FEATURE:
<223> OTHER INFORMATION: amino acid sequence from a VL CDR3 of an
      anti-FXII antibody

<400> SEQUENCE: 15

Ala Ala Trp Asp Ala Ser Leu Arg Gly Val
1               5                   10

<210> SEQ ID NO 16
<211> LENGTH: 10
<212> TYPE: PRT
<213> ORGANISM: Artificial Sequence
<220> FEATURE:
<223> OTHER INFORMATION: amino acid sequence from a VL CDR3 of an
      anti-FXII antibody
<220> FEATURE:
<221> NAME/KEY: X
<222> LOCATION: (2)..(2)
<223> OTHER INFORMATION: A or S
<220> FEATURE:
<221> NAME/KEY: X
<222> LOCATION: (4)..(4)
<223> OTHER INFORMATION: D or Y or E or T or W or S
<220> FEATURE:
<221> NAME/KEY: X
<222> LOCATION: (5)..(5)
<223> OTHER INFORMATION: A or N or I or L or V or P or Q or E
<220> FEATURE:
<221> NAME/KEY: X
<222> LOCATION: (6)..(6)
<223> OTHER INFORMATION: S or D or P or E or Q or R
<220> FEATURE:
<221> NAME/KEY: X
<222> LOCATION: (7)..(7)
<223> OTHER INFORMATION: L or V
<220> FEATURE:
<221> NAME/KEY: X
<222> LOCATION: (9)..(9)
<223> OTHER INFORMATION: G or L or K
<220> FEATURE:
<221> NAME/KEY: X
<222> LOCATION: (10)..(10)
<223> OTHER INFORMATION: V or A or D or T or M or G

<400> SEQUENCE: 16

Ala Xaa Trp Xaa Xaa Xaa Xaa Arg Xaa Xaa
1               5                   10

<210> SEQ ID NO 17
<211> LENGTH: 13
<212> TYPE: PRT
<213> ORGANISM: Artificial Sequence
<220> FEATURE:
<223> OTHER INFORMATION: amino acid sequence from a VL CDR1 of an
``` anti-FXII antibody

<400> SEQUENCE: 17

Ser Gly Ser Ser Glu Met Thr Val His His Tyr Val Tyr
1               5                   10

<210> SEQ ID NO 18
<211> LENGTH: 129
<212> TYPE: PRT
<213> ORGANISM: artificial sequence
<220> FEATURE:
<223> OTHER INFORMATION: amino acid sequence from the VH of anti-FXII
      antibody gVR115

<400> SEQUENCE: 18

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
                20                  25                  30

Ile Met Gln Trp Val Arg Gln Ala Pro Gly Lys Gly Leu Glu Trp Val
            35                  40                  45

Ser Gly Ile Asp Ile Pro Thr Lys Gly Thr Val Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Leu Pro Arg Ser Gly Tyr Leu Ile Ser Pro His Tyr Tyr
            100                 105                 110

Tyr Tyr Ala Leu Asp Val Trp Gly Gln Gly Thr Val Thr Val Ser Ser
        115                 120                 125

Ser

<210> SEQ ID NO 19
<211> LENGTH: 110
<212> TYPE: PRT
<213> ORGANISM: artificial sequence
<220> FEATURE:
<223> OTHER INFORMATION: amino acid sequence from the VL of anti-FXII
      antibody gVR115

<400> SEQUENCE: 19

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Arg Asn
                20                  25                  30

Tyr Val Tyr Trp Tyr Gln Gln Leu Pro Gly Thr Ala Pro Lys Leu Leu
            35                  40                  45

Ile Tyr Ser Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Ala Ser Leu
                85                  90                  95

Arg Gly Val Phe Gly Gly Gly Thr Lys Leu Thr Val Leu Gly
            100                 105                 110

<210> SEQ ID NO 20
<211> LENGTH: 456

```
<212> TYPE: PRT
<213> ORGANISM: artificial sequence
<220> FEATURE:
<223> OTHER INFORMATION: amino acid sequence from the heavy chain of
      anti-FXII antibody gVR115

<400> SEQUENCE: 20
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
            20                  25                  30

Ile Met Gln Trp Val Arg Gln Ala Pro Gly Lys Gly Leu Glu Trp Val
        35                  40                  45

Ser Gly Ile Asp Ile Pro Thr Lys Gly Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Leu Pro Arg Ser Gly Tyr Leu Ile Ser Pro His Tyr Tyr
            100                 105                 110

Tyr Tyr Ala Leu Asp Val Trp Gly Gln Gly Thr Thr Val Thr Val Ser
        115                 120                 125

Ser Ala Ser Thr Lys Gly Pro Ser Val Phe Pro Leu Ala Pro Cys Ser
    130                 135                 140

Arg Ser Thr Ser Glu Ser Thr Ala Ala Leu Gly Cys Leu Val Lys Asp
145                 150                 155                 160

Tyr Phe Pro Glu Pro Val Thr Val Ser Trp Asn Ser Gly Ala Leu Thr
                165                 170                 175

Ser Gly Val His Thr Phe Pro Ala Val Leu Gln Ser Ser Gly Leu Tyr
            180                 185                 190

Ser Leu Ser Ser Val Val Thr Val Pro Ser Ser Ser Leu Gly Thr Lys
        195                 200                 205

Thr Tyr Thr Cys Asn Val Asp His Lys Pro Ser Asn Thr Lys Val Asp
    210                 215                 220

Lys Arg Val Glu Ser Lys Tyr Gly Pro Pro Cys Pro Pro Cys Pro Ala
225                 230                 235                 240

Pro Glu Phe Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser Gln Glu Asp Pro Glu Val Gln Phe Asn Trp Tyr Val
        275                 280                 285

Asp Gly Val Glu Val His Asn Ala Lys Thr Lys Pro Arg Glu Glu Gln
    290                 295                 300

Phe Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Gly
                325                 330                 335

Leu Pro Ser Ser Ile Glu Lys Thr Ile Ser Lys Ala Lys Gly Gln Pro
            340                 345                 350

Arg Glu Pro Gln Val Tyr Thr Leu Pro Pro Ser Gln Glu Glu Met Thr
        355                 360                 365

Lys Asn Gln Val Ser Leu Thr Cys Leu Val Lys Gly Phe Tyr Pro Ser
370                 375                 380

```
Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Arg Leu Thr Val Asp Lys Ser Arg Trp Gln Glu Gly Asn Val Phe
            420                 425                 430

Ser Cys Ser Val Met His Glu Ala Leu His Asn His Tyr Thr Gln Lys
        435                 440                 445

Ser Leu Ser Leu Ser Leu Gly Lys
    450                 455
```

<210> SEQ ID NO 21
<211> LENGTH: 215
<212> TYPE: PRT
<213> ORGANISM: artificial sequence
<220> FEATURE:
<223> OTHER INFORMATION: amino acid sequence from the light chain of anti-FXII antibody gVR115

<400> SEQUENCE: 21

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Arg Asn
            20                  25                  30

Tyr Val Tyr Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Ala Ser Leu
                85                  90                  95

Arg Gly Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215
```

<210> SEQ ID NO 22
<211> LENGTH: 615
<212> TYPE: PRT
<213> ORGANISM: Homo sapiens
<220> FEATURE:
<223> OTHER INFORMATION: amino acid sequence of a human Factor XII

<400> SEQUENCE: 22

```
Met Arg Ala Leu Leu Leu Gly Phe Leu Val Ser Leu Glu Ser
1               5                   10                  15

Thr Leu Ser Ile Pro Pro Trp Glu Ala Pro Lys Glu His Lys Tyr Lys
            20              25                  30

Ala Glu Glu His Thr Val Val Leu Thr Val Thr Gly Glu Pro Cys His
                35                  40                  45

Phe Pro Phe Gln Tyr His Arg Gln Leu Tyr His Lys Cys Thr His Lys
50                      55                  60

Gly Arg Pro Gly Pro Gln Pro Trp Cys Ala Thr Pro Asn Phe Asp
65                  70                  75                  80

Gln Asp Gln Arg Trp Gly Tyr Cys Leu Glu Pro Lys Lys Val Lys Asp
                85                  90                  95

His Cys Ser Lys His Ser Pro Cys Gln Lys Gly Gly Thr Cys Val Asn
            100                 105                 110

Met Pro Ser Gly Pro His Cys Leu Cys Pro Gln His Leu Thr Gly Asn
            115                 120                 125

His Cys Gln Lys Glu Lys Cys Phe Glu Pro Gln Leu Leu Arg Phe Phe
        130                 135                 140

His Lys Asn Glu Ile Trp Tyr Arg Thr Glu Gln Ala Ala Val Ala Arg
145                 150                 155                 160

Cys Gln Cys Lys Gly Pro Asp Ala His Cys Gln Arg Leu Ala Ser Gln
                165                 170                 175

Ala Cys Arg Thr Asn Pro Cys Leu His Gly Gly Arg Cys Leu Glu Val
            180                 185                 190

Glu Gly His Arg Leu Cys His Cys Pro Val Gly Tyr Thr Gly Ala Phe
        195                 200                 205

Cys Asp Val Asp Thr Lys Ala Ser Cys Tyr Asp Gly Arg Gly Leu Ser
    210                 215                 220

Tyr Arg Gly Leu Ala Arg Thr Thr Leu Ser Gly Ala Pro Cys Gln Pro
225                 230                 235                 240

Trp Ala Ser Glu Ala Thr Tyr Arg Asn Val Thr Ala Glu Gln Ala Arg
                245                 250                 255

Asn Trp Gly Leu Gly Gly His Ala Phe Cys Arg Asn Pro Asp Asn Asp
            260                 265                 270

Ile Arg Pro Trp Cys Phe Val Leu Asn Arg Asp Arg Leu Ser Trp Glu
        275                 280                 285

Tyr Cys Asp Leu Ala Gln Cys Gln Thr Pro Thr Gln Ala Ala Pro Pro
    290                 295                 300

Thr Pro Val Ser Pro Arg Leu His Val Pro Leu Met Pro Ala Gln Pro
305                 310                 315                 320

Ala Pro Pro Lys Pro Gln Pro Thr Thr Arg Thr Pro Gln Ser Gln
                325                 330                 335

Thr Pro Gly Ala Leu Pro Ala Lys Arg Glu Gln Pro Pro Ser Leu Thr
            340                 345                 350

Arg Asn Gly Pro Leu Ser Cys Gly Gln Arg Leu Arg Lys Ser Leu Ser
        355                 360                 365

Ser Met Thr Arg Val Val Gly Gly Leu Val Ala Leu Arg Gly Ala His
    370                 375                 380

Pro Tyr Ile Ala Ala Leu Tyr Trp Gly His Ser Phe Cys Ala Gly Ser
385                 390                 395                 400

Leu Ile Ala Pro Cys Trp Val Leu Thr Ala Ala His Cys Leu Gln Asp
            405                 410                 415

Arg Pro Ala Pro Glu Asp Leu Thr Val Val Leu Gly Gln Glu Arg Arg
```

```
                420             425             430
Asn His Ser Cys Glu Pro Cys Gln Thr Leu Ala Val Arg Ser Tyr Arg
            435             440             445

Leu His Glu Ala Phe Ser Pro Val Ser Tyr Gln His Asp Leu Ala Leu
    450             455             460

Leu Arg Leu Gln Glu Asp Ala Asp Gly Ser Cys Ala Leu Leu Ser Pro
465             470             475             480

Tyr Val Gln Pro Val Cys Leu Pro Ser Gly Ala Ala Arg Pro Ser Glu
                485             490             495

Thr Thr Leu Cys Gln Val Ala Gly Trp Gly His Gln Phe Glu Gly Ala
            500             505             510

Glu Glu Tyr Ala Ser Phe Leu Gln Glu Ala Gln Val Pro Phe Leu Ser
            515             520             525

Leu Glu Arg Cys Ser Ala Pro Asp Val His Gly Ser Ser Ile Leu Pro
            530             535             540

Gly Met Leu Cys Ala Gly Phe Leu Glu Gly Gly Thr Asp Ala Cys Gln
545             550             555             560

Gly Asp Ser Gly Gly Pro Leu Val Cys Glu Asp Gln Ala Ala Glu Arg
                565             570             575

Arg Leu Thr Leu Gln Gly Ile Ile Ser Trp Gly Ser Gly Cys Gly Asp
            580             585             590

Arg Asn Lys Pro Gly Val Tyr Thr Asp Val Ala Tyr Tyr Leu Ala Trp
            595             600             605

Ile Arg Glu His Thr Val Ser
            610             615
```

<210> SEQ ID NO 23
<211> LENGTH: 609
<212> TYPE: PRT
<213> ORGANISM: Homo sapiens
<220> FEATURE:
<223> OTHER INFORMATION: amino acid sequence of a mature form of human
      albumin

<400> SEQUENCE: 23

```
Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
    50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160
```

-continued

```
Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
    210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
        275                 280                 285

Cys Glu Asn Gln Asp Ser Ile Ser Ser Lys Leu Lys Glu Cys Cys Glu
    290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Val
        355                 360                 365

Leu Leu Leu Arg Leu Ala Lys Thr Tyr Glu Thr Thr Leu Glu Lys Cys
    370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415

Glu Leu Phe Glu Gln Leu Gly Glu Tyr Lys Phe Gln Asn Ala Leu Leu
            420                 425                 430

Val Arg Tyr Thr Lys Lys Val Pro Gln Val Ser Thr Pro Thr Leu Val
        435                 440                 445

Glu Val Ser Arg Asn Leu Gly Lys Val Gly Ser Lys Cys Cys Lys His
    450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
            500                 505                 510

Ser Ala Leu Glu Val Asp Glu Thr Tyr Val Pro Lys Glu Phe Asn Ala
        515                 520                 525

Glu Thr Phe Thr Phe His Ala Asp Ile Cys Thr Leu Ser Glu Lys Glu
    530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
```

```
                580                 585                 590
Ala Glu Glu Gly Lys Lys Leu Val Ala Ala Ser Gln Ala Ala Leu Gly
        595                 600                 605
Leu

<210> SEQ ID NO 24
<211> LENGTH: 12
<212> TYPE: PRT
<213> ORGANISM: Artificial Sequence
<220> FEATURE:
<223> OTHER INFORMATION: amino acid sequence of an Infestin-4 variant

<400> SEQUENCE: 24

Val Arg Asn Pro Cys Ala Cys Phe Arg Asn Tyr Val
1               5                   10

<210> SEQ ID NO 25
<211> LENGTH: 12
<212> TYPE: PRT
<213> ORGANISM: Artificial Sequence
<220> FEATURE:
<223> OTHER INFORMATION: amino acid sequence of an Infestin-4 variant

<400> SEQUENCE: 25

Asp Ser Leu Gly Arg Glu Val Arg Asn Pro Cys Ala
1               5                   10
```